(12) United States Patent
Zoller et al.

(10) Patent No.: US 8,673,917 B2
(45) Date of Patent: Mar. 18, 2014

(54) 2-HETEROARYL-PYRROLO [3,4-C]PYRROLE DERIVATIVES, AND USE THEREOF AS SCD INHIBITORS

(75) Inventors: Gerhard Zoller, Schöneck (DE); Marc Dietrich Voss, Frankfurt am Main (DE); Hans Matter, Frankfurt am Main (DE); Andreas Herling, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/063,088

(22) PCT Filed: Sep. 2, 2009

(86) PCT No.: PCT/EP2009/006333
§ 371 (c)(1),
(2), (4) Date: Aug. 30, 2011

(87) PCT Pub. No.: WO2010/028761
PCT Pub. Date: Mar. 18, 2010

(65) Prior Publication Data
US 2012/0028986 A1    Feb. 2, 2012

(30) Foreign Application Priority Data
Sep. 9, 2008   (EP) .................................... 08290845

(51) Int. Cl.
| | | |
|---|---|---|
| *C07D 401/14* | (2006.01) | |
| *A61K 31/4402* | (2006.01) | |
| *A61K 31/501* | (2006.01) | |
| *A61P 3/00* | (2006.01) | |
| *A61P 3/04* | (2006.01) | |
| *A61P 3/10* | (2006.01) | |
| *A61P 9/00* | (2006.01) | |

(52) U.S. Cl.
USPC .... 514/252.06; 514/338; 544/238; 546/276.7

(58) Field of Classification Search
USPC ............ 544/238; 514/252.06, 338; 546/276.7
See application file for complete search history.

(56) References Cited

U.S. PATENT DOCUMENTS

2010/0144594 A1   6/2010   Zoller et al.
2012/0190692 A1*  7/2012   Bunnelle et al. ......... 514/255.05

FOREIGN PATENT DOCUMENTS

| WO | WO 2005/011653 A2 | 2/2005 |
| WO | WO 2005/011656 A2 | 2/2005 |
| WO | WO 2006/086445 A2 | 8/2006 |
| WO | WO 2008/135141 A1 | 11/2008 |

OTHER PUBLICATIONS

Ortinau, et al., International Scholarly Research Network Endocrinology, vol. 2012, Article ID 947323, 11 pages.*
Brown, et al., Curr Opin Lipidol. Jun. 2010 ; 21(3): 192-197.*
International Preliminary Report on Patentability dated Mar. 15, 2011.
International Search Report dated Nov. 10, 2009.
Hulver, Matthew, W., et al., "Elevated stearoyl-CoA desaturase-1 expression in skeletal muscle contributes to abnormal fatty acid partitioning in obese humans", Cell Metabolism, vol. 2, pp. 251-261, Oct. 2005.
Warensjo, E., et al., "Fatty acid composition of serum lipids predicts the development of the metabolic syndrome in men", Diabetologia, (2005) 48; 1999-2005.

* cited by examiner

*Primary Examiner* — James O Wilson
*Assistant Examiner* — Cecilia M Jaisle
(74) *Attorney, Agent, or Firm* — Scully, Scott, Murphy & Presser, P.C.

(57) ABSTRACT

The invention relates to compounds of the formula (I), where the groups R1, M, A, B, D, L, and R have the specified meanings, and to the physiologically compatible salts thereof. The compounds are suitable, for example, for treating metabolic syndrome, insulin resistance, obesity, and diabetes.

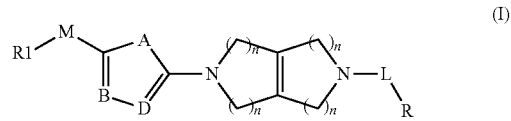

11 Claims, No Drawings

2-HETEROARYL-PYRROLO [3,4-C]PYRROLE DERIVATIVES, AND USE THEREOF AS SCD INHIBITORS

The invention relates to heterocyclic derivatives and physiologically compatible salts thereof.

Structurally similar compounds and the use thereof as SCD1 inhibitors have already been described.

It was an object of the invention to provide novel compounds which display a therapeutically utilizable action. More particularly, the object consisted in finding novel compounds which are suitable for treatment of elevated lipid concentrations in the blood and in tissue, metabolic syndrome, obesity, especially visceral (abdominal) obesity, including the prevention of the sequelae associated therewith, diabetes, insulin resistance, dysregulation of LDL, HLD and VLDL, or cardiovascular disorders.

The invention therefore relates to compounds of the formula I

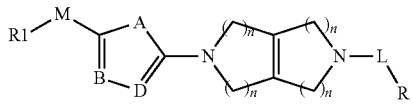

I in which
R is hydrogen, $(C_1-C_{16})$-alkyl, $(C_1-C_5)$-alkyloxy, $(C_1-C_5)$-alkylthio, $(C_1-C_5)$-alkylamino, di-$(C_2-C_8)$-alkylamino, $(C_0-C_4)$-alkylene-$(C_6-C_{10})$-aryl, $(C_0-C_4)$-alkylene-$(C_5-C_{12})$-heteroaryl, $(C_0-C_4)$-alkylene-$(C_3-C_{12})$-heterocyclyl, $(C_0-C_4)$-alkylene-$(C_3-C_{12})$-cycloalkyl, a bicyclic $(C_8-C_{14})$ ring system,
where aryl, heteroaryl, heterocyclyl, cycloalkyl or the bicyclic $(C_8-C_{14})$ ring system may be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl or aminosulfonyl;
R1 is hydrogen, $(C_1-C_{10})$-alkyl, —$(C_6-C_{10})$-aryl, —$(C_5-C_{12})$-heteroaryl, —$(C_3-C_{12})$-heterocyclyl, —$(C_3-C_{12})$-cycloalkyl;
where alkyl may be substituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, —$(C_6-C_{10})$-aryl, —$(C_5-C_{12})$-heteroaryl, —$(C_3-C_{12})$-heterocyclyl or —$(C_3-C_{12})$-cycloalkyl,
where aryl, heteroaryl, heterocyclyl or cycloalkyl may optionally be mono- or polysubstituted by halogen, $(C_1-C_6)$-alkyl, $(C_1-C_3)$-alkyloxy, hydroxyl, $(C_1-C_6)$-alkyl-mercapto, amino, $(C_1-C_6)$-alkylamino, di-$(C_2-C_{12})$-alkylamino;
R2 is hydrogen, $(C_1-C_{16})$-alkyl, $(C_0-C_4)$-alkylene-$(C_6-C_{10})$-aryl;
R3 is hydrogen, $(C_1-C_6)$-alkyl, $(C_1-C_3)$-alkyloxy, hydroxyl, $(C_1-C_6)$-alkyl-mercapto, amino, $(C_1-C_6)$-alkylamino, di-$(C_2-C_{12})$-alkylamino, cyano, $(C_1-C_6)$-alkylcarbonyl, halogen, trifluoromethyl, trifluoromethyloxy, $(C_1-C_6)$-alkylsulfonyl, aminosulfonyl;
A is O, S, N(R2), C(R3), C(R3)=C(R3);
B is C(R3), N;
D is C(R3), N;
where at least one of the members A, B or D must be nitrogen;
L is a bond, —C(=O)—, —C(=S)—, —C(=O)—N(R2)-, —C(=O)—O—, —S(O)$_{0-2}$—, —S(O)$_{0-2}$—N(R2)-, a mono- or bicyclic ring system in which one or more ring members may be N(R3), O, S or —C(=O)—:
M is —O—, —O—CH$_2$—;
n is in each case independently 1 or 2;
and physiologically compatible salts thereof.

Preference is given to compounds of the formula I where n equals 1, which gives rise to the compounds of the formula Ia

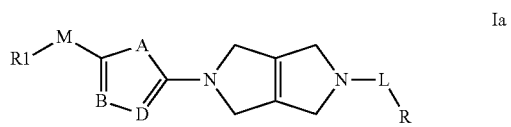

Ia in which
R is hydrogen, $(C_1-C_{16})$-alkyl, $(C_1-C_5)$-alkyloxy, $(C_1-C_5)$-alkylthio, $(C_1-C_5)$-alkylamino, di-$(C_2-C_8)$-alkylamino, $(C_0-C_4)$-alkylene-$(C_6-C_{10})$-aryl, $(C_0-C_4)$-alkylene-$(C_5-C_{12})$-heteroaryl, $(C_0-C_4)$-alkylene-$(C_3-C_{12})$-heterocyclyl, $(C_0-C_4)$-alkylene-$(C_3-C_{12})$-cycloalkyl, a bicyclic $(C_8-C_{14})$ ring system,
where aryl, heteroaryl, heterocyclyl, cycloalkyl or the bicyclic $(C_8-C_{14})$ ring system may be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl or aminosulfonyl;
R1 is $(C_1-C_{10})$-alkyl, —$(C_6-C_{10})$-aryl; —$(C_5-C_{12})$-heteroaryl, —$(C_3-C_{12})$-heterocyclyl, —$(C_3-C_{12})$-cycloalkyl,
where alkyl may be substituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, —$(C_6-C_{10})$-aryl, —$(C_5-C_{12})$-heteroaryl, —$(C_3-C_{12})$-heterocyclyl or —$(C_3-C_{12})$-cycloalkyl,
where aryl, heteroaryl, heterocyclyl or cycloalkyl may optionally be mono- or polysubstituted by halogen, $(C_1-C_6)$-alkyl, $(C_1-C_3)$-alkyloxy, hydroxyl, $(C_1-C_6)$-alkyl-mercapto, amino, $(C_1-C_6)$-alkylamino, di-$(C_2-C_{12})$-alkylamino;
R2 is hydrogen, $(C_1-C_{16})$-alkyl, $(C_0-C_4)$-alkylene-$(C_6-C_{10})$-aryl;
R3 is hydrogen, $(C_1-C_6)$-alkyl, $(C_1-C_3)$-alkyloxy, hydroxyl, $(C_1-C_6)$-alkyl-mercapto, amino, $(C_1-C_6)$-alkylamino, di-$(C_2-C_{12})$-alkylamino, cyano, $(C_1-C_6)$-alkylcarbonyl, halogen, trifluoromethyl, trifluoromethyloxy, $(C_1-C_6)$-alkylsulfonyl, aminosulfonyl;
A is O, S, N(R2), C(R3), C(R3)=C(R3);
B is C(R3), N;
D is C(R3), N;
where at least one of the members A, B or D must be nitrogen;
L is a bond, —C(=O)—, —C(=S)—, —C(=O)—N(R2)-, —C(=O)—O—, —S(O)$_{0-2}$—, —S(O)$_{0-2}$—N(R2)-, a mono- or bicyclic ring system in which one or more ring members may be N(R3), O, S or —C(=O)—:
M is —O—, —O—CH$_2$—;
and physiologically compatible salts thereof.

Particular preference is given to compounds of the formula Ia

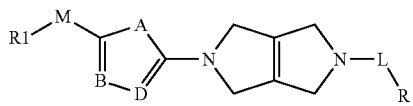

in which
R is hydrogen, $(C_1-C_{16})$-alkyl, $(C_1-C_5)$-alkyloxy, $(C_1-C_5)$-alkylthio, $(C_1-C_5)$-alkylamino, di-$(C_2-C_8)$-alkylamino, $(C_0-C_4)$-alkylene-$(C_6-C_{10})$-aryl, $(C_0-C_4)$-alkylene-$(C_5-C_{12})$-heteroaryl, $(C_0-C_4)$-alkylene-$(C_3-C_{12})$-heterocyclyl, $(C_0-C_4)$-alkylene-$(C_3-C_{12})$-cycloalkyl, a bicyclic $(C_8-C_{14})$ ring system,
where aryl, heteroaryl, heterocyclyl, cycloalkyl or the bicyclic $(C_8-C_{14})$ ring system may be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl or aminosulfonyl;

R1 is $(C_1-C_{10})$-alkyl, —$(C_6-C_{10})$-aryl, —$(C_5-C_{12})$-heteroaryl, —$(C_3-C_{12})$-heterocyclyl, —$(C_3-C_{12})$-cycloalkyl,
where alkyl may be substituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, —$(C_6-C_{10})$-aryl, —$(C_5-C_{12})$-heteroaryl, —$(C_3-C_{12})$-heterocyclyl or —$(C_3-C_{12})$-cycloalkyl,
where aryl, heteroaryl, heterocyclyl or cycloalkyl may optionally be mono- or polysubstituted by halogen, $(C_1-C_6)$-alkyl, $(C_1-C_3)$-alkyloxy, hydroxyl, $(C_1-C_6)$-alkyl-mercapto, amino, $(C_1-C_6)$-alkylamino, di-$(C_2-C_{12})$-alkylamino;

R2 is hydrogen, $(C_1-C_{16})$-alkyl, $(C_0-C_4)$-alkylene-$(C_6-C_{10})$-aryl;
R3 is hydrogen, $(C_1-C_6)$-alkyl, $(C_1-C_3)$-alkyloxy, hydroxyl, $(C_1-C_6)$-alkyl-mercapto, amino, $(C_1-C_6)$-alkylamino, di-$(C_2-C_{12})$-alkylamino, cyano, $(C_1-C_6)$-alkylcarbonyl, halogen, trifluoromethyl, trifluoromethyloxy, $(C_1-C_6)$-alkylsulfonyl, aminosulfonyl;
A is S, C(R3)=C(R3);
B is C(R3), N;
D is N;
L is a bond, —C(=O)—, —C(=S)—, —C(=O)—N(R2)-, —C(=O)—O—, —S(O)$_{0-2}$—, —S(O)$_{0-2}$—N(R2)-, a mono- or bicyclic ring system in which one or more ring members may be N(R3), O, S or —C(=O)—:
M is —O—, —O—CH$_2$;
and physiologically compatible salts thereof.

Very particular preference is given to compounds of the formula Ia,

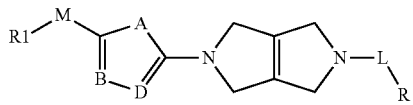

in which
R is $(C_1-C_{16})$-alkyl, $(C_1-C_5)$-alkyloxy, $(C_0-C_4)$-alkylene-$(C_6-C_{10})$-aryl, a bicyclic $(C_8-C_{14})$ ring system,
where aryl or the bicyclic $(C_8-C_{14})$ ring system may be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkylcarbonyl, $(C_1-C_6)$-alkylcarbonyl, cyano, trifluoromethyl, trifluoromethyloxy, $(C_1-C_6)$-alkylsulfonyl or aminosulfonyl;

R1 is $(C_1-C_{10})$-alkyl, —$(C_6-C_{10})$-aryl, —$(C_5-C_{12})$-heteroaryl, —$(C_3-C_{12})$-heterocyclyl, —$(C_3-C_{12})$-cycloalkyl,
where alkyl may be substituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, —$(C_6-C_{10})$-aryl, —$(C_5-C_{12})$-heteroaryl, —$(C_3-C_{12})$-heterocyclyl or —$(C_3-C_{12})$-cycloalkyl,
where aryl, heteroaryl, heterocyclyl or cycloalkyl may optionally be mono- or polysubstituted by halogen, $(C_1-C_6)$-alkyl, $(C_1-C_3)$-alkyloxy, hydroxyl, $(C_1-C_6)$-alkyl-mercapto, amino, $(C_1-C_6)$-alkylamino, di-$(C_2-C_{12})$-alkylamino;

R2 is hydrogen, $(C_1-C_{16})$-alkyl, $(C_0-C_4)$-alkylene-$(C_6-C_{10})$-aryl;
R3 is hydrogen, $(C_1-C_6)$-alkyl, $(C_1-C_3)$-alkyloxy, hydroxyl, $(C_1-C_6)$-alkyl-mercapto, amino, $(C_1-C_6)$-alkylamino, di-$(C_2-C_{12})$-alkylamino, cyano, $(C_1-C_6)$-alkylcarbonyl, halogen, trifluoromethyl, trifluoromethyloxy, $(C_1-C_6)$-alkylsulfonyl, aminosulfonyl;
A is C(R3)=C(R3);
B is C(R3), N;
D is N;
L is a bond, —C(=O)—:
M is —O—;
and physiologically compatible salts thereof.

Also very particularly preferred are compounds of the formula Ia

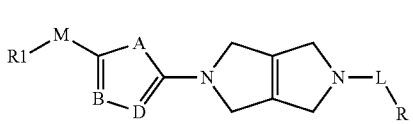

in which
R is $(C_0-C_4)$-alkylene-$(C_6-C_{10})$-aryl,
where aryl may be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl or aminosulfonyl;

R1 is $(C_0-C_4)$-alkylene-$(C_6-C_{10})$-aryl, $(C_0-C_4)$-alkylene-$(C_5-C_{12})$-heteroaryl,
where aryl or heteroaryl may optionally be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino;
R3 is hydrogen;
A is C(R3)=C(R3);
B is C(R3), N;
D is N;

L is —C(=O)—;
M is —O—;
and physiologically compatible salts thereof.

Also very particularly preferred are compounds of the formula Iaa

<chemical structure, formula Iaa> in which
R1 is (C$_0$-C$_4$)-alkylene-(C$_6$-C$_{10}$)-aryl, (C$_0$-C$_4$)-alkylene-(C$_5$-C$_{12}$)-heteroaryl,
where aryl or heteroaryl may optionally be mono- or polysubstituted by halogen, (C$_1$-C$_6$)-alkyl, (C$_1$-C$_3$)-alkyloxy, hydroxyl, (C$_1$-C$_6$)-alkylmercapto, amino, (C$_1$-C$_6$)-alkylamino, di-(C$_2$-C$_{12}$)-alkylamino;
B is CH, N;
and physiologically compatible salts thereof.

Also very particularly preferred are compounds of the formula Iaa
in which
R1 is (C$_1$-C$_4$)-alkylenephenyl, (C$_1$-C$_4$)-alkylene-(C$_5$-C$_6$)-heteroaryl, where heteroaryl is a monocyclic aromatic ring with one or two ring heteroatoms selected from N, O or S and
where phenyl or heteroaryl may optionally be mono- or polysubstituted by halogen, (C$_1$-C$_6$)-alkyl, (C$_1$-C$_3$)-alkyloxy, hydroxyl, (C$_1$-C$_6$)-alkylmercapto, amino, (C$_1$-C$_6$)-alkylamino, di-(C$_2$-C$_{12}$)-alkylamino;
B is CH, N;
and physiologically compatible salts thereof.

In one embodiment, preference is given to compounds of the formula I in which n in each case is 1.

In one embodiment, preference is given to compounds of the formula I in which L is C=O.

In one embodiment, preference is given to compounds of the formula I in which M is —O—.

In one embodiment, preference is given to compounds of the formula I in which M is —O—CH$_2$—.

In one embodiment, preference is given to compounds of the formula I in which: A is S, D is N and B is CH.

In one embodiment, preference is given to compounds of the formula I in which: A is C(R3)=C(R3), D is N and B is CH.

In one embodiment, preference is given to compounds of the formula I in which: A is CH=CH, D is N and B is CH.

In one embodiment, preference is given to compounds of the formula I in which: A is C(R3)=C(R3), D is N and B is N.

In one embodiment, preference is given to compounds of the formula I in which: A is CH=CH, D is N and B is N.

The invention relates to compounds of the formula I in the form of their salts, racemates, racemic mixtures and pure enantiomers, and their diastereomers and mixtures thereof.

The alkyl radicals in the substituents R, R1, R2 and R3 may either be straight-chain or branched.

Halogen is fluorine, chlorine, bromine or iodine, especially fluorine or chlorine.

Aryl is a monocyclic or bicyclic aromatic hydrocarbon radical which has from 6 to 10 ring atoms and may independently be substituted by from one to four, preferably one or two, substituents described.

Heteroaryl is a monocyclic or bicyclic radical which has from 5 to 12 ring atoms and at least one aromatic ring having one, two or three ring heteroatoms selected from N, O and S, where the remaining ring atoms are C.

Cycloalkyl is a saturated or partly unsaturated ring system (which contains exclusively carbon atoms) which comprises one or more rings.

Heterocyclyl is a saturated or partly unsaturated ring system (which contains at least one heteroatom) which comprises one or more rings.

Bicyclyl is a bicyclic saturated or partly unsaturated ring system, where the individual members of the ring systems may contain exclusively carbon atoms or one, two or three ring heteroatoms selected from N, O and S, the remaining ring atoms being C. One of the rings in the bicyclic system may also be a fused aromatic ring such as benzene.

The definition —(C$_0$)-alkylene- is understood to mean a bond.

When radicals or substituents may occur more than once in the compounds of the formula I (for example "n"), they may all independently be defined as specified and be the same or different.

Owing to their higher water solubility compared to the starting compounds or base compounds, physiologically compatible salts are particularly suitable for medical applications. The salts must have a physiologically compatible anion or cation. Suitable physiologically compatible acid addition salts of the inventive compounds are salts of inorganic acids, such as sulfuric acid, hydrobromic acid, phosphoric acid, metaphosphoric acid, nitric acid, sulfonic acid and sulfuric acid, and also organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. For medical purposes, particular preference is given to using the chlorine salt. Suitable physiologically compatible basic salts are ammonium salts, alkali metal salts (such as sodium and potassium salts), alkaline earth metal salts (such as magnesium and calcium salts), zinc salts, trometamol (2-amino-2-hydroxymethyl-1,3-propanediol) salts, diethanolamine salts, lysine salts, arginine salts, choline salts, meglumine salts or ethylenediamine salts.

Salts with a physiologically incompatible anion or cation are likewise within the scope of the invention as useful intermediates for the preparation or purification of physiologically compatible salts and/or for use in nontherapeutic applications, for example in vitro applications.

A further aspect of this invention is prodrugs of the inventive compounds. Such prodrugs can be metabolized in vivo to give an inventive compound. These prodrugs may themselves be active or inactive.

The inventive compounds may also be present in different polymorphic forms, for example as amorphous and crystalline polymorphic forms. All polymorphic forms of the inventive compounds are within the scope of the invention and are a further aspect of the invention.

Hereinafter, all references to "compound(s) of the formula (I)" refer to compound(s) of the formula (I) as described above, and salts thereof as described herein.

The compounds of the formula I and their physiologically compatible salts and physiologically functional derivatives are ideal medicaments for treatment of elevated lipid concentrations in the blood and in tissue, metabolic syndrome, obesity, diabetes, insulin resistance, dysregulation of LDL, HLD and VLDL, or cardiovascular disorders, lipid metabolism disorders, especially of hyperlipidemia.

The compound(s) of the formula (I) may also be administered in combination with further active ingredients.

The amount of a compound of the formula (I) which is required in order to achieve the desired biological effect is dependent on a series of factors, for example the selected specific compound, the intended use, the method of administration and the clinical condition of the patient. In general, the daily dose is in the range from 0.1 mg to 100 mg (typically from 0.1 mg to 50 mg) per day per kilogram of bodyweight, e.g. 0.1-10 mg/kg/day. Tablets or capsules may, for example, contain from 0.01 to 100 mg, typically from 0.02 to 50 mg. For prophylaxis or therapy of the conditions mentioned above, the compounds of the formula (I) may themselves be used as the compound, but they are preferably present in the form of a pharmaceutical composition with a compatible carrier. The carrier must of course be compatible, in the sense that it is compatible with the other constituents of the composition and is not harmful to the health of the patient. The carrier may be a solid or liquid or both and is preferably formulated with the compound as an individual dose, for example as a tablet, which may contain from 0.05% to 95% by weight of the active ingredient. Further pharmaceutically active substances may likewise be present, including further compounds of the formula (I). The inventive pharmaceutical compositions may be produced by one of the known pharmaceutical methods, which consist essentially in mixing the constituents with pharmacologically compatible carriers and/or assistants.

Inventive pharmaceutical compositions are those which are suitable for oral and peroral (for example sublingual) administration, although the most suitable mode of administration depends in each individual case on the nature and severity of the condition to be treated and on the type of the compound of formula (I) used in each case. Coated formulations and coated slow-release formulations are also encompassed by the scope of the invention. Preference is given to acid- and gastric fluid-resistant formulations. Suitable gastric fluid-resistant coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units, for example capsules, cachets, lozenges or tablets, each of which contains a certain amount of the compound of the formula (I); as powder or granules; as solution or suspension in an aqueous or non-aqueous liquid; or as an oil-in-water or water-in-oil emulsion. These compositions may, as already mentioned, be prepared by any suitable pharmaceutical method which includes a step in which the active ingredient and the carrier (which may consist of one or more additional constituents) are brought into contact. In general, the compositions are prepared by uniform and homogeneous mixing of the active ingredient with a liquid carrier and/or finely divided solid carrier, after which the product is shaped if necessary. For example, a tablet can thus be produced by compressing or shaping a powder or granules of the compound, optionally with one or more additional constituents. Compressed tablets can be prepared by tableting the compound in free-flowing form, for example a powder or granules, optionally mixed with a binder, lubricant, inert diluent and/or one (or more) surfactants/dispersants in a suitable machine. Shaped tablets can be prepared by shaping the pulverulent compound moistened with an inert liquid diluent in a suitable machine.

Pharmaceutical compositions which are suitable for peroral (sublingual) administration include lozenges which contain a compound of formula (I) with a flavoring, customarily sucrose, and gum arabic or tragacanth, and pastilles which include the compound in an inert base, such as gelatin and glycerol or sucrose and gum arabic.

Combinations with Other Medicaments

The inventive compounds can be administered alone or in combination with one or more further pharmacologically active ingredients which have, for example, favorable effects on metabolic disturbances or disorders frequently associated therewith.

Examples of such medicaments are
1. medicaments which lower blood glucose, antidiabetics,
2. active ingredients for the treatment of dyslipidemias,
3. antiatherosclerotic medicaments,
4. antiobesity agents,
5. antiinflammatory active ingredients,
6. active ingredients for the treatment of malignant tumors,
7. antithrombotic active ingredients,
8. active ingredients for the treatment of high blood pressure,
9. active ingredients for the treatment of heart failure and
10. active ingredients for the treatment and/or prevention of complications caused by diabetes or associated with diabetes.

They can be combined with the inventive compounds of the formula (I), in particular for a synergistic improvement in the effect. Administration of the active ingredient combination can take place either by separate administration of the active ingredients to the patient or in the form of combination products in which a plurality of active ingredients are present in one pharmaceutical preparation.

Suitable further active ingredients for the combination products are especially: All antidiabetics which are mentioned in the Rote Liste 2006, Chapter 12; all slimming agents/appetite suppressants which are mentioned in the Rote Liste 2005, Chapter 1; all lipid reducers which are mentioned in the Rote Liste 2006, Chapter 58. They can be combined with the inventive compound of the formula I especially for synergistic improvement of action. The active ingredient combination can be administered either by separate addition of the active ingredients to the patient or in the form of combination preparations in which a plurality of active ingredients are present in a pharmaceutical formulation. Most of the active ingredients mentioned below are disclosed in USP Dictionary of USAN and International Drug Names, US Pharmacopeia, Rockville 2001.

Antidiabetics include insulin and insulin derivatives, for example Lantus® (see www.lantus.com) or HMR 1964 or those as described in WO2005005477 (Novo Nordisk), fast-acting insulins (see U.S. Pat. No. 6,221,633), inhalable insulins, for example Exubera®, or oral insulins, for example IN-105 (Nobex) or Oral-lyn™ (Generex Biotechnology), GLP-1 derivatives, for example exenatide, liraglutide or those which have been disclosed in WO 98/08871, WO2005027978 by Novo Nordisk A/S, in WO 01/04156 by Zealand or in WO 00/34331 by Beaufour-Ipsen, pramlintide acetate (Symlin; Amylin Medicaments), and orally active hypoglycemic ingredients.

The orally active hypoglycemic ingredients preferably include
sulfonylureas,
biguanidines,
meglitinides,
oxadiazolidinediones,
thiazolidinediones,
glucosidase inhibitors,
inhibitors of glycogen phosphorylase,
glucagon antagonists, glucokinase activators,
inhibitors of fructose 1,6-bisphosphatase,
modulators of glucose transporter 4 (GLUT4),
inhibitors of glutamine:fructose-6-phosphate amidotransferase (GFAT),
GLP-1 agonists, potassium channel openers, for example those which have been disclosed in WO 97/26265 and WO 99/03861 by Novo Nordisk A/S,
inhibitors of dipeptidylpeptidase-IV (DPP-IV),
insulin sensitizers,
inhibitors of liver enzymes which are involved in the stimulation of gluconeogenesis and/or glycogenolysis,
modulators of glucose uptake, of glucose transport and of glucose absorption,
inhibitors of 11β-HSD1,
inhibitors of protein-tyrosine phosphatase 1B (PTP1B),
modulators of the sodium-dependent glucose transporter 1 or 2 (SGLT1, SGLT2),
lipid metabolism-modifying compounds, such as active antihyperlipidemic ingredients and active antilipidemic ingredients,
compounds which reduce nutrient intake,
compounds which increase thermogenesis,
PPAR and RXR modulators and
active ingredients which act on the ATP-dependent potassium channel of the beta cells.

In one embodiment of the invention, the compounds of the formula I are administered in combination with an HMG-CoA reductase inhibitor such as simvastatin, fluvastatin, pravastatin, lovastatin, atorvastatin, cerivastatin, rosuvastatin, L659699.

In one embodiment of the invention, the compound of the formula I is administered in combination with a cholesterol absorption inhibitor, for example ezetimibe, tiqueside, pamaqueside, FM-VP4 (sitostanol/campesterol ascorbyl phosphate; Forbes Medi-Tech, WO2005042692), MD-0727 (Microbia Inc., WO2005021497), or with compounds as described in WO2002066464 (Kotobuki Pharmaceutical Co. Ltd.) or WO2005062824 (Merck & Co.) or WO2005061451 and WO2005061452 (AstraZeneca AB).

In one embodiment of the invention, the compound of the formula I is administered in combination with a PPAR gamma agonist, for example rosiglitazone, pioglitazone, JTT-501, GI 262570, R-483, CS-011 (rivoglitazone).

In one embodiment of the invention, the compound of the formula I is administered in combination with a PPAR alpha agonist, for example GW9578, GW-590735, K-111, LY-674, KRP-101, DRF-10945.

In one embodiment of the invention, the compound of the formula I is administered in combination with a mixed PPAR alpha/gamma agonist, for example muraglitazar, tesaglitazar, naveglitazar, LY-510929, ONO-5129, E-3030, AVE 8042, AVE 8134, AVE 0847, or as described in PCT/US 00/11833, PCT/US 00/11490, DE10142734.4 or in J. P. Berger et al., TRENDS in Pharmacological Sciences 28(5), 244-251, 2005.

In one embodiment of the invention, the compound of the formula I is administered in combination with a PPAR delta agonist, for example GW-501516.

In one embodiment, the compound of the formula I is administered in combination with metaglidasen or with MBX-2044 or other partial PPAR gamma agonists/antagonists.

In one embodiment of the invention, the compound of the formula I is administered in combination with a fibrate, for example fenofibrate, clofibrate, bezafibrate.

In one embodiment of the invention, the compound of the formula I is administered in combination with an MTP inhibitor, for example implitapide, BMS-201038, R-103757, or those as described in WO2005085226.

In one embodiment of the invention, the compound of the formula I is administered in combination with a CETP inhibitor, for example torcetrapib or JTT-705.

In one embodiment of the invention, the compound of the formula I is administered in combination with bile acid absorption inhibitors (see, for example, U.S. Pat. Nos. 6,245,744, 6,221,897 or WO00/61568), for example HMR 1741, or those as described in DE 10 2005 033099.1 and DE 10 2005 033100.9.

In one embodiment of the invention, the compound of the formula I is administered in combination with a polymeric bile acid adsorber, for example cholestyramine, colesevelam.

In one embodiment of the invention, the compound of the formula I is administered in combination with an LDL receptor inducer (see U.S. Pat. No. 6,342,512), for example HMR1171, HMR1586, or those as described in WO2005097738.

In one embodiment, the compound of the formula I is administered in combination with Omacor® (omega-3 fatty acids; highly concentrated ethyl esters of eicosapentaenoic acid and of docosahexaenoic acid).

In one embodiment of the invention, the compound of the formula I is administered in combination with an ACAT inhibitor, for example avasimibe.

In one embodiment of the invention, the compound of the formula I is administered in combination with an antioxidant, for example OPC-14117, probucol, tocopherol, ascorbic acid, β-carotene or selenium.

In one embodiment of the invention, the compound of the formula I is administered in combination with a vitamin, for example vitamin B6 or vitamin B12.

In one embodiment of the invention, the compound of the formula I is administered in combination with a lipoprotein lipase modulator, for example ibrolipim (NO-1886).

In one embodiment of the invention, the compound of the formula I is administered in combination with an ATP-citrate lyase inhibitor, for example SB-204990.

In one embodiment of the invention, the compound of the formula I is administered in combination with a squalene synthetase inhibitor, for example BMS-188494, or as described in WO2005077907.

In one embodiment of the invention, the compound of the formula I is administered in combination with a lipoprotein (a) antagonist, for example gemcabene (CI-1027).

In one embodiment of the invention, the compound of the formula I is administered in combination with an HM74A receptor agonist, for example nicotinic acid.

In one embodiment of the invention, the compound of the formula I is administered in combination with a lipase inhibitor, for example orlistat or cetilistat (ATL-962).

In one embodiment of the invention, the compound of the formula I is administered in combination with insulin.

In one embodiment, the compound of the formula I is administered in combination with a sulfonylurea, for example tolbutamide, glibenclamide, glipizide or glimepiride.

In one embodiment, the compound of the formula I is administered in combination with a biguanide, for example metformin.

In another embodiment, the compound of the formula I is administered in combination with a meglitinide, for example repaglinide or nateglinide.

In one embodiment, the compound of the formula I is administered in combination with a thiazolidinedione, for example troglitazone, ciglitazone, pioglitazone, rosiglitazone, or the compounds disclosed in WO 97/41097 of Dr. Reddy's Research Foundation, especially 5-[[4-[(3,4-dihydro-3-methyl-4-oxo-2-quinazolinyl)methoxy]phenyl]methyl]-2,4-thiazolidinedione.

In one embodiment, the compound of the formula I is administered in combination with an α-glucosidase inhibitor, for example miglitol or acarbose.

In one embodiment, the compound of the formula I is administered in combination with an active ingredient which acts on the ATP-dependent potassium channel of the beta cells, for example tolbutamide, glibenclamide, glipizide, glimepiride or repaglinide.

In one embodiment, the compound of the formula I is administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932.

In one embodiment, the compound of the formula I is administered in combination with glucagon receptor antagonists, for example A-770077 or NNC-25-2504, or as described in WO2004100875, WO2005065680.

In one embodiment, the compound of the formula I is administered in combination with activators of glucokinase, for example LY-2121260 (WO2004063179), PSN-105, PSN-110, GKA-50, or those as described, for example, in WO2004072031 or WO2004072066 or WO2005080360.

In one embodiment, the compound of the formula I is administered in combination with an inhibitor of gluconeogenesis, for example FR-225654.

In one embodiment, the compound of the formula I is administered in combination with inhibitors of fructose-1,6-bisphosphatase (FBPase), for example CS-917.

In one embodiment, the compound of the formula I is administered in combination with modulators of glucose transporter 4 (GLUT4), for example KST-48 (D.-O. Lee et al.: Arzneim.-Forsch. Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidylpeptidase IV (DPP-IV), for example vildagliptin (LAF-237), sitagliptin (MK-0431), saxagliptin (BMS-477118), GSK-823093, PSN-9301, SYR-322, SYR-619, TA-6666, TS-021, GRC-8200, GW-825964X, or as described in WO2003074500, WO2003106456, WO200450658, WO2005058901, WO2005012312, WO2005/012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment, the compound of the formula I is administered in combination with inhibitors of 11-beta-hydroxysteroid dehydrogenase 1 (11β-HSD1), for example BVT-2733, or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004065351, WO2004089367, WO2004089380, WO2004089470-71, WO2004089896, WO2005016877, WO2005097759.

In one embodiment, the compound of the formula I is administered in combination with inhibitors of protein tyrosine phosphatase 1B (PTP1B), as described, for example, in WO200119830-31, WO200117516, WO2004506446, WO2005012295, PCT/EP2005/005311, PCT/EP2005/005321, PCT/EP2005/007151, PCT/EP2005/ or DE 10 2004 060542.4.

In one embodiment, the compound of the formula I is administered in combination with modulators of the sodium-dependent glucose transporter 1 or 2 (SGLT1, SGLT2), for example KGA-2727, T-1095, SGL-0010, AVE 2268 and SAR 7226, or as described, for example, in WO2004007517, WO200452903, WO200452902, PCT/EP2005/005959, WO2005085237, JP2004359630, or by A. L. Handlon in Expert Opin. Ther. Patents (2005) 15(11), 1531-1540.

In one embodiment, the compound of the formula I is administered in combination with modulators of GPR40.

In one embodiment, the compound of the formula I is administered in combination with inhibitors of hormone-sensitive lipase (HSL), as described, for example, in WO2005073199.

In one embodiment, the compound of the formula I is administered in combination with inhibitors of acetyl-CoA carboxylase (ACC), for example those as described in WO199946262, WO200372197, WO2003072197, WO2005044814.

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of glycogen synthase kinase-3 beta (GSK-3 beta), as described, for example, in US2005222220, WO2005085230, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117.

In one embodiment, the compound of the formula I is administered in combination with an inhibitor of protein kinase C beta (PKC beta), for example ruboxistaurin.

In one embodiment, the compound of the formula I is administered in combination with an endothelin-A receptor antagonist, for example avosentan (SPP-301).

In one embodiment, the compound of the formula I is administered in combination with inhibitors of "I kappaB kinase" (IKK inhibitors), as described, for example, in WO2001000610, WO2001030774, WO2004022553, WO2005097129.

In one embodiment, the compound of the formula I is administered in combination with modulators of the glucocorticoid receptor, as described, for example, in WO2005090336.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example N-{4-[(4-aminoquinazolin-2-ylamino)methyl]cyclohexyl-methyl}naphthalene-1-sulfonamide hydrochloride (CGP 71683A);

peptide YY 3-36 (PYY3-36) or analogous compounds, for example CJC-1682 (PYY3-36 conjugated to human serum albumin via Cys34) or CJC-1643 (derivative of PYY3-36, which is conjugated to serum albumin in vivo) or those as described in WO2005080424;

cannabinoid receptor 1 antagonists (for example rimonabant, SR147778, or those as described, for example, in EP 0656354, WO 00/15609, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897);

MC4 agonists (e.g. N-[2-(3a-benzyl-2-methyl-3-oxo-2,3,3a,4,6,7-hexahydropyrazolo-[4,3-c]pyridin-5-yl)-1-(4-chlorophenyl)-2-oxoethyl]-1-amino-1,2,3,4-tetrahydronaphthalene-2-carboxamide (WO 01/91752)) or LB53280, LB53279, LB53278 or THIQ, MB243, RY764, CHIR-785, PT-141 or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076, WO2004072077;

orexin receptor antagonists (e.g. 1-(2-methylbenzoxazol-6-yl)-3-[1,5]haphthyridin-4-ylurea hydrochloride (SB-334867-A) or those as described, for example, in WO200196302, WO200185693, WO2004085403, WO2005075458); histamine H3 receptor agonists (e.g. 3-cyclohexyl-1-(4,4-dimethyl-1,4,6,7-tetrahydro-imidazo[4,5-c]pyridin-5-yl)propan-1-one oxalic acid salt (WO 00/63208) or those as described in WO200064884, WO2005082893);

CRF antagonists (e.g. [2-methyl-9-(2,4,6-trimethylphenyl)-9H-1,3,9-triazafluoren-4-yl]-dipropylamine (WO 00/66585));

CRF BP antagonists (e.g. urocortin);

urocortin agonists;

β3 agonists (for example 1-(4-chloro-3-methanesulfonyl-methylphenyl)-2-[2-(2,3-dimethyl-1H-indol-6-yloxy)ethylamino]ethanol hydrochloride (WO 01/83451));

MSH (melanocyte-stimulating hormone) agonists;

MCH (melanine-concentrating hormone) receptor antagonists (for example NBI-845, A-761, A-665798, A-798, ATC-0175, T-226296, T-71, GW-803430 or those compounds as described in WO2003/15769, WO2005085200, WO2005019240, WO2004011438, WO2004012648, WO2003015769, WO2004072025, WO2005070898, WO2005070925, WO2004039780, WO2003033476, WO2002006245, WO2002002744, WO2003004027, FR2868780);

CCK-A agonists (for example {2-[4-(4-chloro-2,5-dimethoxyphenyl)-5-(2-cyclohexyl-ethyl)thiazol-2-ylcarbamoyl]-5,7-dimethylindol-1-yl}acetic acid trifluoroacetic acid salt (WO 99/15525) or SR-146131 (WO 0244150) or SSR-125180);

serotonin reuptake inhibitors (e.g. dexfenfluramine);

mixed serotoninergic and noradrenergic compounds (e.g. WO 00/71549);

5-HT receptor agonists, e.g. 1-(3-ethylbenzofuran-7-yl)piperazine oxalic acid salt (WO 01/09111);

5-HT2C receptor agonists (for example APD-356 or BVT-933 or those as described in WO200077010, WO20077001-02, WO2005019180, WO2003064423, WO200242304, WO2005082859);

5-HT6 receptor antagonists, as described, for example, in WO2005058858;

bombesin receptor agonists (BRS-3 agonists);

galanin receptor antagonists;

growth hormone (e.g. human growth hormone or AOD-9604);

growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695));

growth hormone secretagogue receptor antagonists (ghrelin antagonists), for example A-778193 or those as described in WO2005030734;

TRH agonists (see, for example, EP 0 462 884);

decoupling protein 2 or 3 modulators;

leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

DA agonists (bromocriptin, doprexin);

lipase/amylase inhibitors (e.g. WO 00/40569);

inhibitors of diacylglycerol O-acyltransferases (DGATs), as described, for example, in US2004/0224997, WO2004094618, WO200058491, WO2005044250, WO2005072740, JP2005206492, WO2005013907;

inhibitors of fatty acid synthase (FAS), for example C75 or those as described in WO2004005277;

oxyntomodulin;

oleoyl-estrone;

or agonists of the thyroid hormone receptor (thyroid hormone receptor agonists), for example: KB-2115 or those as described in WO20058279, WO200172692, WO200194293, WO2003084915, WO2004018421, WO2005092316.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindole or phentermin.

In one embodiment, the compound of the formula I is administered in combination with dietary fiber, preferably insoluble dietary fiber (see, for example, Carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höchst, 65926 Frankfurt/Main). The combination with Caromax® can be effected in one formulation, or by separate administration of compounds of the formula I and Caromax®. Caromax® can also be administered in the form of foods, for example in bakery products or muesli bars.

It will be appreciated that any suitable combination of the inventive compounds with one or more of the aforementioned compounds and optionally one or more further pharmacologically active substances is considered to fall within the scope of protection of the present invention.

FM-VP4

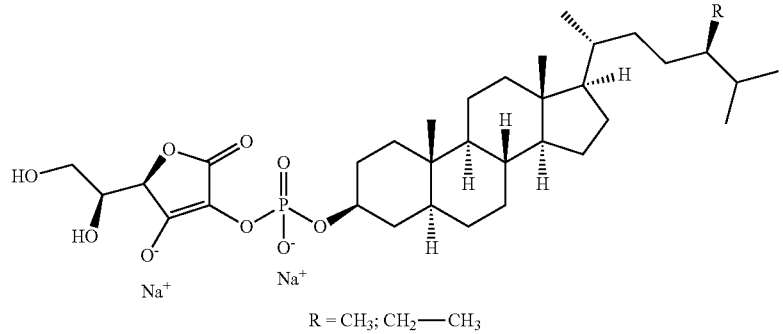

R = CH₃; CH₂—CH₃

JTT-501

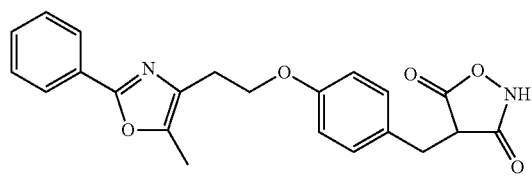

GI 262570

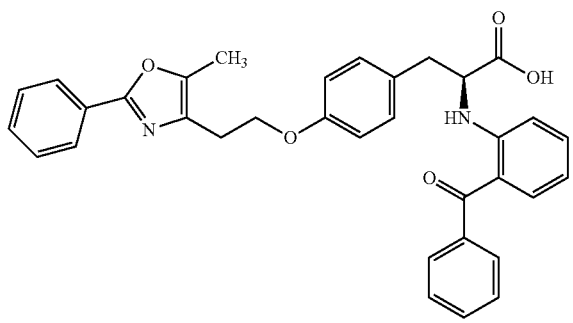

CS-011

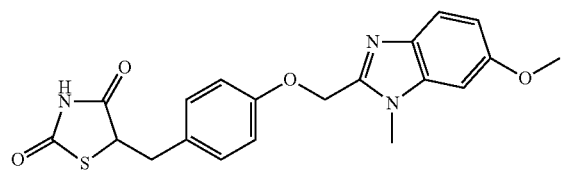

Rivoglitazone

GW-9578

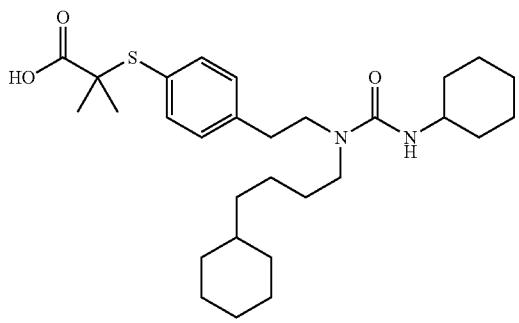

K-11

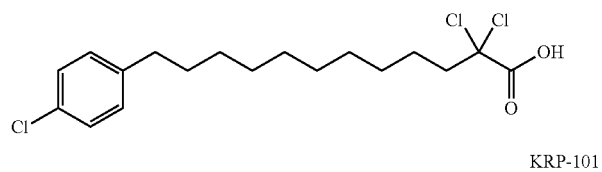

LY-674

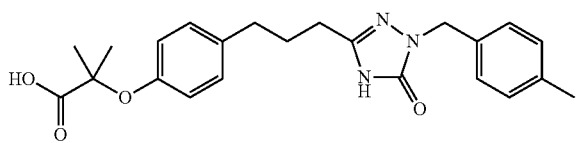

KRP-101

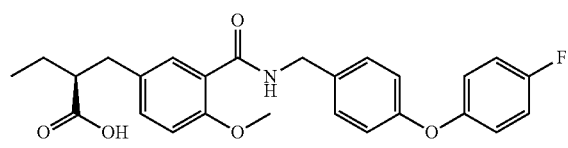

LY-510929

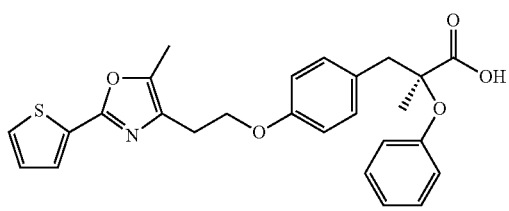

-continued
GW-501516
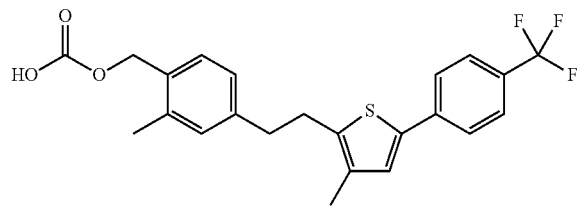
BMS-201038
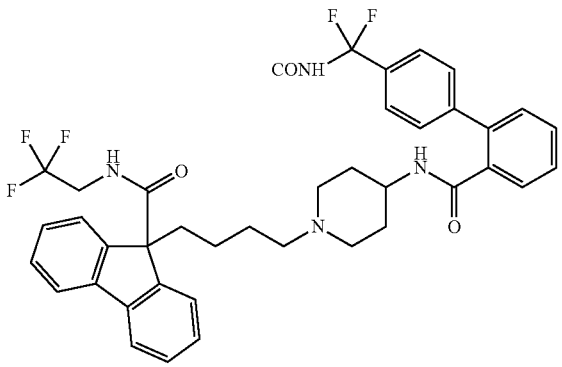
R-103757
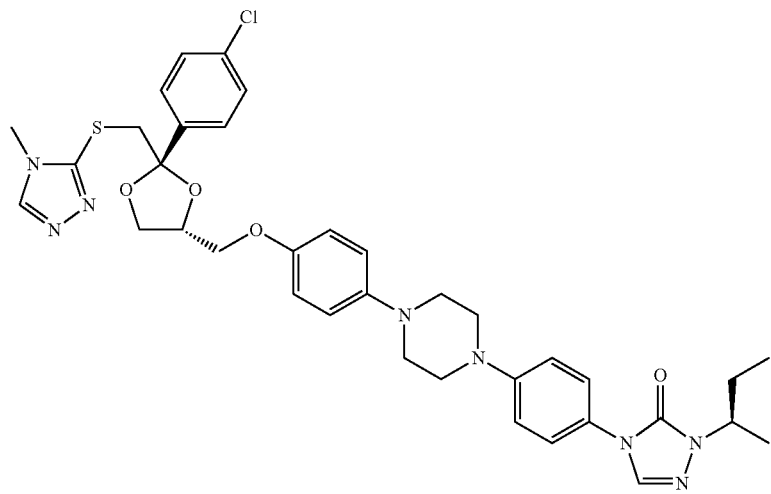
JTT-705
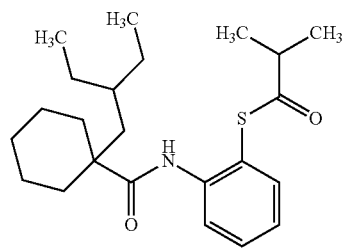
OPC-14117
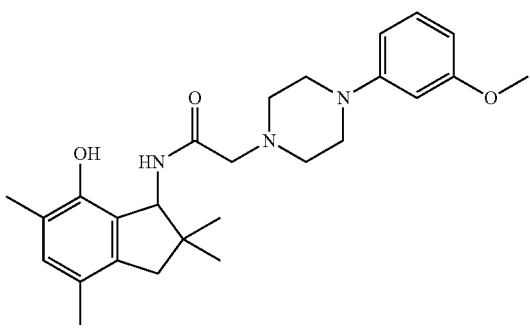
NO-1886
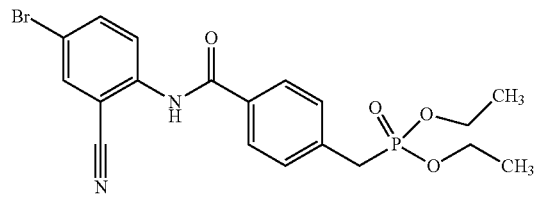
SB-204990
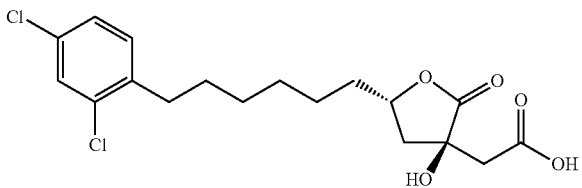

-continued
BMS-188494
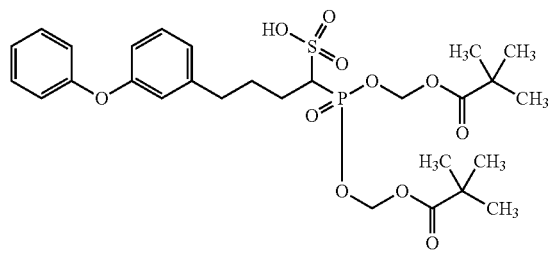
CI-1027
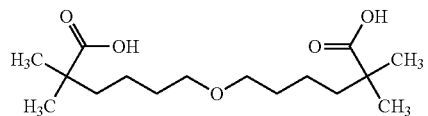
ATL-962
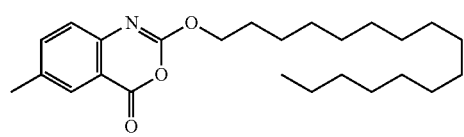
FR-258900
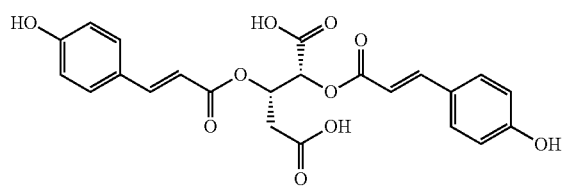
NNC-25-2504
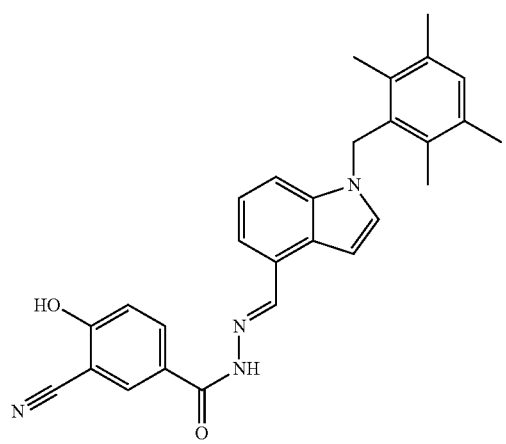
LY-2121260
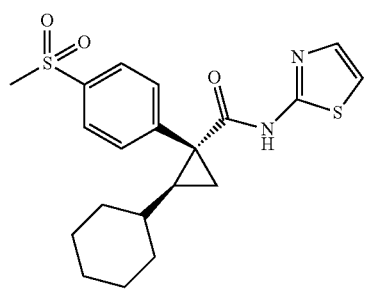
GKA-50
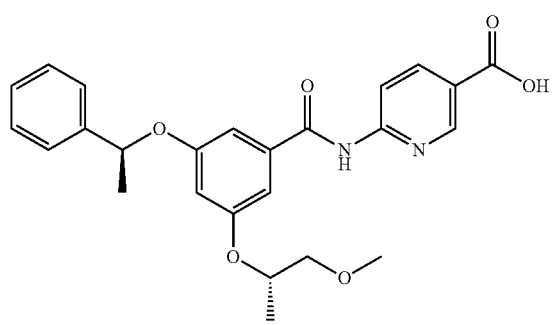
FR-225654
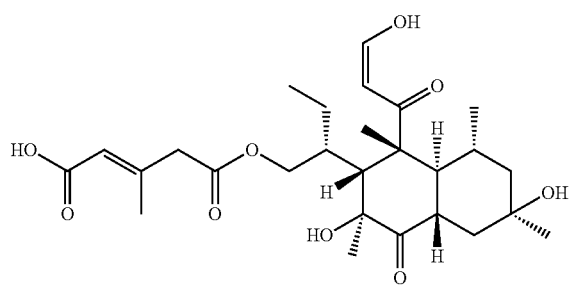
KST-48
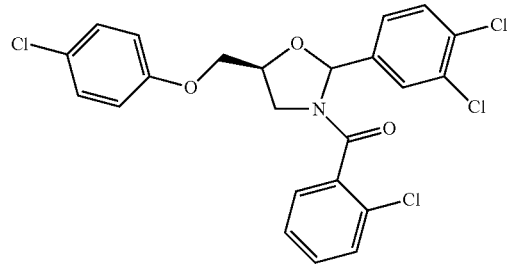
BMS-477118

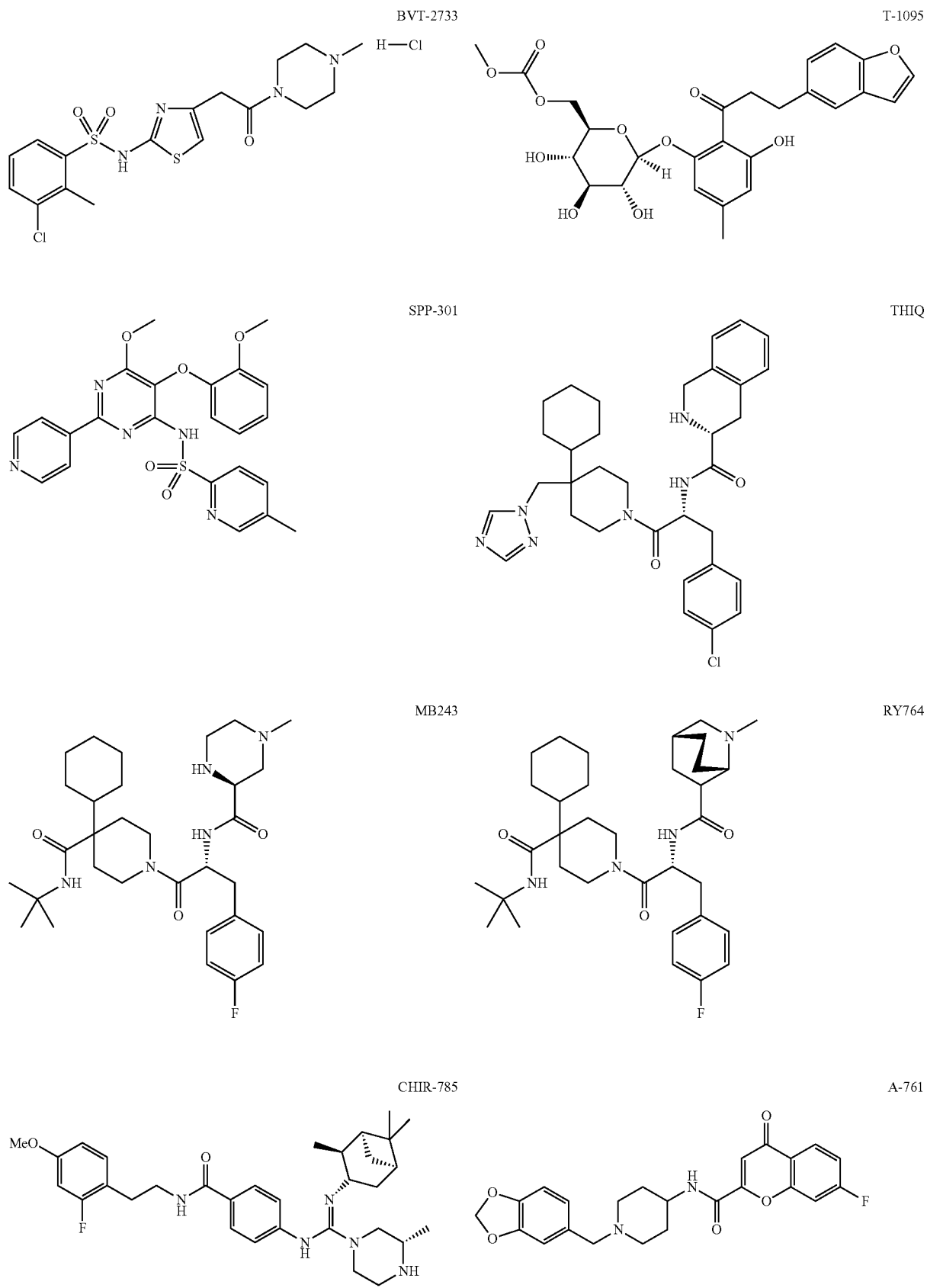

-continued
A-665798
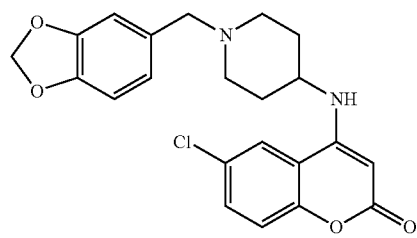
ATC-0175
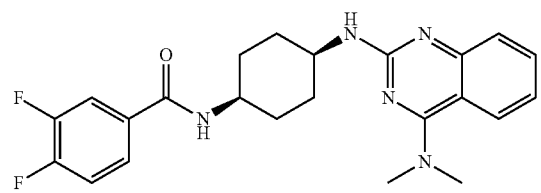
T-226296
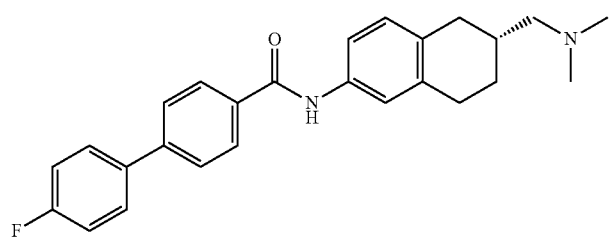
GW-803430
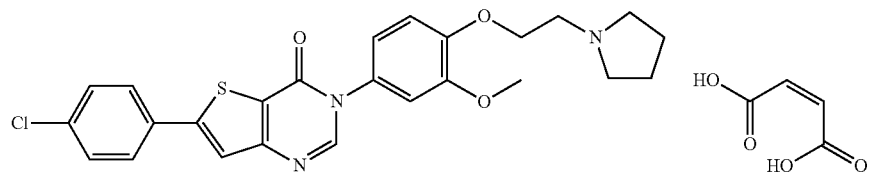
AOD-9604
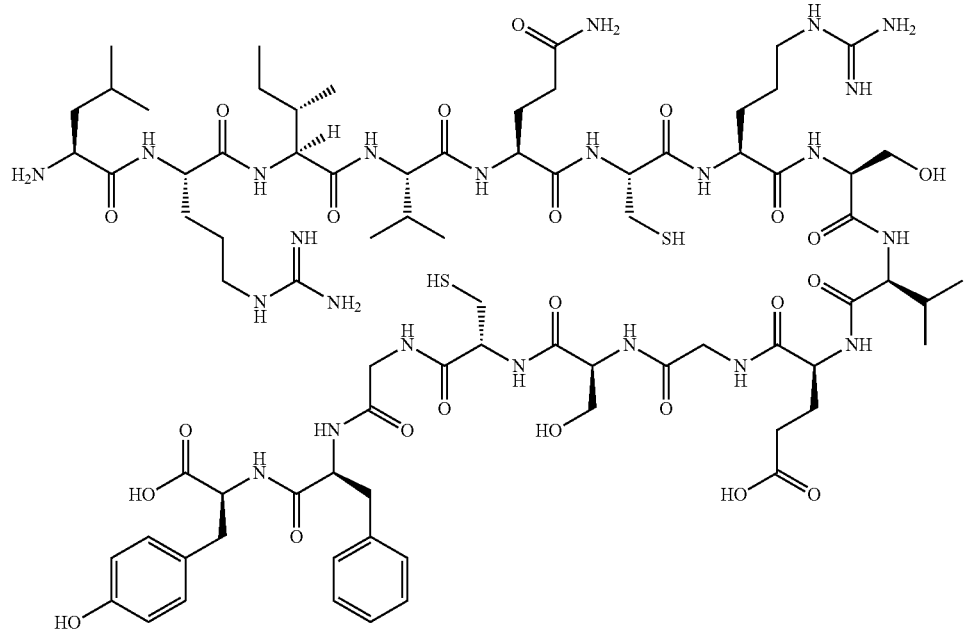
A-778193
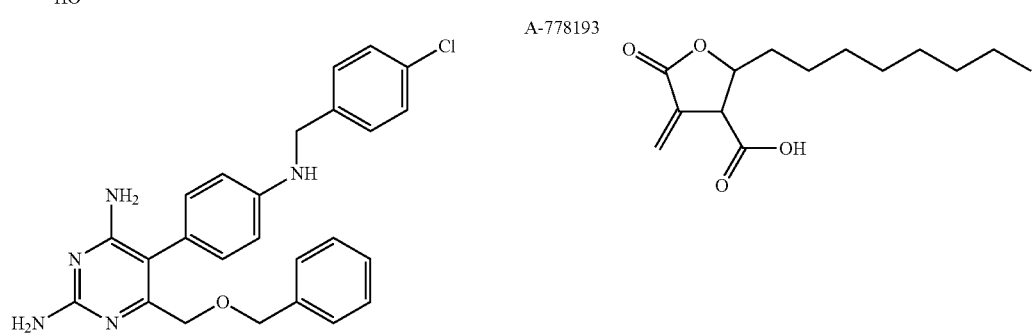
C75
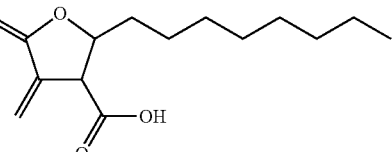

-continued

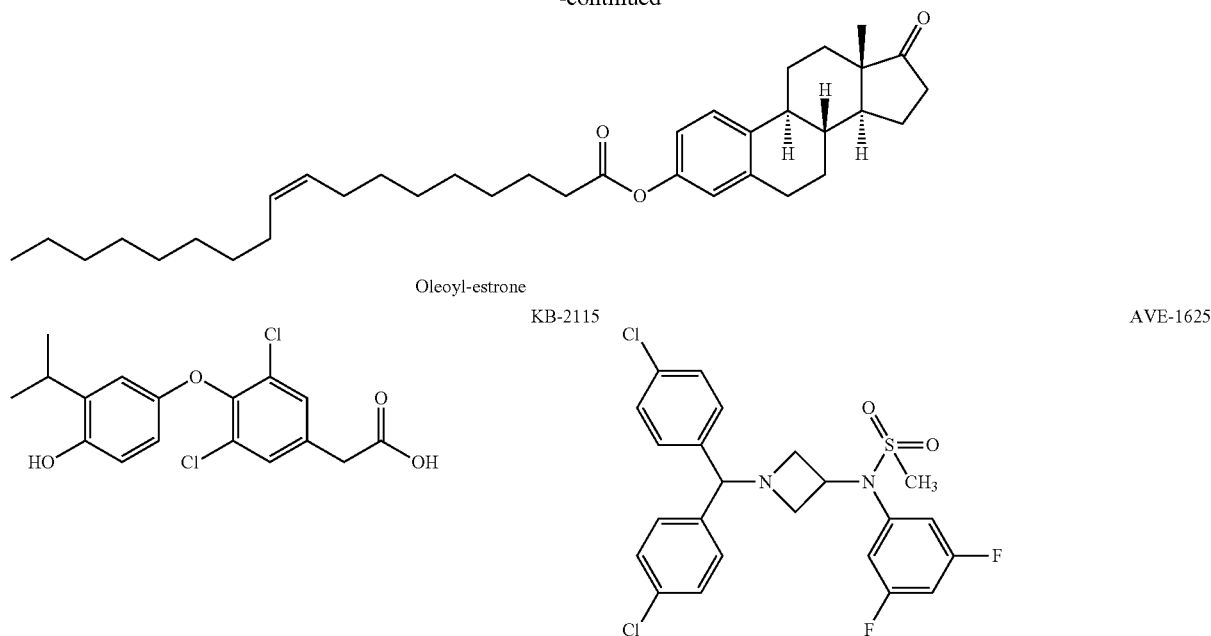

Oleoyl-estrone

KB-2115

AVE-1625

The invention further provides both stereoisomer mixtures of the formula I and the pure stereoisomers of the formula I, and also diastereomer mixtures of the formula I and the pure diastereomers. The mixtures are separated by a chromatographic method.

The examples which follow serve to illustrate the invention in detail, without restricting it to the products and embodiments described in the examples.

The efficacy of the inventive compounds of the formula I was tested with microsomal enzymes in the following assay system:

The livers of male Wistar rats which (to induce the expression of SCD1) had been fed with a carbohydrate-rich, low-fat diet were homogenized with a Potter tissue homogenizer and differential centrifugation in a buffer which contained 250 mM/l of sucrose and 5 mM/l of HEPES (pH 7.0). The resuspended microsome fraction was stored at −80° C. The stearoyl-CoA desaturase activity was determined in a thin-film chromatography assay with 1-$^{14}$C-labeled stearic acid. In short, the particular inventive compounds (in DMSO in a final concentration of 1% [v/v]) were incubated with 15 µg of the rat liver microsomes in 200 µl of assay buffer (6 mM/l of MgCl$_2$, 250 mM/l of sucrose, 150 mM/l of KCl, 40 mM/l of NaF, 100 mM/l of Na$_2$HPO$_4$ (pH7.4), 1.3 mM/l of ATP, 1.5 mM/l of reduced glutathione, 60 uM/l of CoA, 0.33 mM/l of nicotinamide and 0.94 mM/l of NADH) at room temperature for 10 min. 0.5 µCi [1-$^{14}$C]-stearic acid (55 mCi/mmol) was added, and the mixture was incubated at 37° C. for 1 h. The radioactively labeled fatty acids were subsequently hydrolyzed at 65° C. with 2.5 M KOH/MeOH:H$_2$O (4:1) for 4 h, protonated with 280 µl of formic acid and extracted with 500 µl of hexane. The TLC plates were immersed into 10% AgNO$_3$ and heat-activated before use. 150 µl of the hexane phase were applied to the plates, and the TLC plates were developed in buffer (chloroform:methanol:acetic acid:water [90:8:1:0.8]) and dried. The plates were read off in a phosphoimager to quantify the SCD1 activity.

The person skilled in the art can modify this assay in various aspects to determine the inhibition of the stearoyl-CoA desaturase activity. Representative inventive compounds like those described in the examples showed, when tested in this assay at a concentration of 10 µM/l, activity as inhibitors of SCD1, which is reported as inhibition of SCD1 activity in percent, or in the test of different concentrations as the IC50, reported in mol/l.

TABLE 2

| Biological activity | |
|---|---|
| Ex. | % inhibition (10 µM) |
| 1 | 80 |
| 2 | 86 |
| 3 | 100 |

TABLE 3

| Biological activity | |
|---|---|
| Ex. | IC50 (mol/l) |
| 1 | 1.33E−07 |
| 2 | 7.95E−07 |
| 3 | 7.18E−09 |
| 4 | 4.34E−08 |
| 5 | 2.13E−07 |
| 6 | 4.83E−07 |
| 7 | 7.12E−06 |
| 8 | 8.48E−09 |
| 9 | 1.34E−06 |

The compounds of the formula I inhibit the SCD1 activity and are therefore very suitable for treating metabolic disorders, obesity and metabolic syndrome (Hulver et al. Cell Metabolism (2005), 2(4), 251-261 and Warensjoe et al. Diabetologia (2005), 48(10), 1999-2005).

Owing to the inhibition of the SCD activity, the compounds of the formula I can also be used for treatment or prevention of further diseases mediated by SCD or a condition mediated by SCD in a mammal, preferably a human.

The compounds of the present invention are suitable especially for treatment and/or prevention of:
1. Obesity, especially visceral (abdominal) obesity
2. Disorders of fatty acid metabolism and glucose utilization disorders
    Disorders in which insulin resistance is involved
3. Diabetes mellitus, especially type 2 diabetes, including the prevention of the sequelae associated therewith. Particular aspects in this connection are
    hyperglycemia,
    improvement in insulin resistance,
    improvement in glucose tolerance,
    protection of the pancreatic β cells
    prevention of macro- and microvascular disorders
4. Dyslipidemias and their sequelae such as, for example, atherosclerosis, coronary heart disease, cerebrovascular disorders etc, especially those (but not restricted thereto) which are characterized by one or more of the following factors:
    high plasma triglyceride concentrations, high postprandial plasma triglyceride concentrations,
    low HDL cholesterol concentration
    low apoA lipoprotein concentrations
    high LDL cholesterol concentrations
    small dense LDL cholesterol particles
    high apoB lipoprotein concentrations
    desaturation index (e.g. ratio 18:1/18:0n-9, 16:1/16:0n-7 or 18:1n-9+16:1n-7/16:0 fatty acids)
5. Various other conditions which may be associated with metabolic syndrome or syndrome X, such as:
    increased abdominal girth
    dyslipidemia (e.g. hypertriglyceridemia and/or low HDL)
    insulin resistance
    hypercoagulability
    hyperuricemia
    microalbuminemia
    thromboses, hypercoagulable and prothrombotic states (arterial and venous)
    high blood pressure
    heart failure such as, for example (but not restricted thereto), following myocardial infarction, hypertensive heart disease or cardiomyopathy
6. Hepatic disorders and conditions related thereto
    fatty liver
    hepatic steatosis
    non-alcoholic hepatitis
    non-alcoholic steatohepatitis (NASH)
    alcoholic hepatitis
    acute fatty liver
    fatty liver of pregnancy
    drug-induced hepatitis
    iron overload disorders
    hepatic fibrosis
    hepatic cirrhosis
    hepatoma
    viral hepatitis
7. Skin disorders and conditions and those associated with polyunsaturated fatty acids
    eczema
    acne
    psoriasis
    keloid scar formation or prevention
    other diseases related to mucous membrane fatty acid composition
8. Primary hypertriglyceridemia or secondary hypertriglyceridemias following
    familial histiocytic reticulosis
    lipoprotein lipase deficiency
    hyperlipoproteinemias
    apolipoprotein deficiency (e.g. apoCII or apoE deficiency)
9. Diseases or conditions related to neoplastic cellular proliferation
    benign or malignant tumors
    cancer
    neoplasia
    metastases
    carcinogenesis
10. Diseases or conditions related to neurological, psychiatric or immune disorders or conditions
11. Other diseases or conditions in which inflammatory reactions, cell differentiation and/or other aspects mediated by SCD may for example be involved are:
    atherosclerosis such as, for example (but not restricted thereto), coronary sclerosis including angina pectoris or myocardial infarction, stroke, ischemic stroke and transient ischemic attack (TIA)
    peripheral occlusive disease
    vascular restenosis or reocclusion
    chronic inflammatory bowel diseases such as, for example, Crohn's disease and ulcerative colitis
    pancreatitis
    sinusitis
    other inflammatory conditions
    retinopathy, ischemic retinopathy
    adipose cell tumors
    lipomatous carcinomas such as, for example, liposarcomas
    solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
    acute and chronic myeloproliferative disorders and lymphomas
    angiogenesis
    neurodegenerative disorders
    Alzheimer's disease
    multiple sclerosis
    Parkinson's disease
    erythemato-squamous dermatoses such as, for example, psoriasis
    acne vulgaris
    other skin disorders and dermatological conditions which are modulated by PPAR
    eczemas and neurodermatitis
    dermatitis such as, for example, seborrheic dermatitis or photodermatitis
    keratitis and keratoses such as, for example, seborrheic keratoses, senile keratoses, actinic keratosis, photo-induced keratoses or keratosis follicularis
    keloids and keloid prophylaxis
    warts, including condylomata or condylomata acuminata
    human papilloma viral (HPV) infections such as, for example, venereal papillomata, viral warts such as, for example, molluscum contagiosum, leukoplakia
    papular dermatoses such as, for example, lichen planus
    skin cancer such as, for example, basal-cell carcinomas, melanomas or cutaneous T-cell lymphomas
    localized benign epidermal tumors such as, for example, keratoderma, epidermal naevi
    chilblains high blood pressure
syndrome X
polycystic ovary syndrome (PCOS)
asthma
cystic fibrosis
osteoarthritis
lupus erythematosus (LE) or inflammatory rheumatic disorders such as, for example, rheumatoid arthritis
vasculitis
wasting (cachexia)
gout
ischemia/reperfusion syndrome
acute respiratory distress syndrome (ARDS)
viral diseases and infections
lypodystrophy and lipodystrophic conditions, also for treating adverse drug effects (e.g. after taking medicaments for treating HIV or tumors)
myopathies and lipid myopathies (such as carnitine palmitoyltransferase I or II deficiency)
Development of Muscles and a Slim Body or Muscle Mass Formation in Animal Husbandry and in Humans
Preparation The inventive compounds of the general formula I are prepared by processes known per se in the literature and are obtainable by the following methods, in which the radicals are each defined as follows:

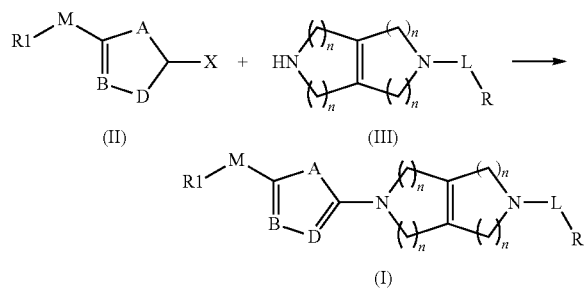

The halogen atom in the heterocycle unit (II) has been replaced by exchange with the amine unit, and then, for example, the M-R1 group can be modified further. If M-R1 is an ester group, it can be reduced and the hydroxymethyl derivatives thus obtained can be alkylated or arylated. In order to modify the L-R group of the amine unit, the reaction sequence is suitably modified, and a combined component (IV) is synthesized, and the different substituents are introduced in the last step.

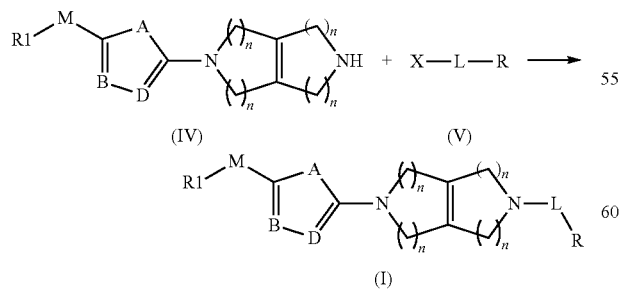

Since acids are usually released in these reactions, it is advantageous for acceleration to add bases such as pyridine, triethylamine, sodium hydroxide solution or alkali metal carbonates. The reactions can be carried out within wide temperature ranges. It has been found to be advantageous to work at temperatures from 0° C. up to the boiling point of the solvent used. Examples of solvents used are methylene chloride, THF, DMF, toluene, ethyl acetate, n-heptane, dioxane, diethyl ether or pyridine. Under anhydrous conditions, strong bases such as lithium hydride, sodium hydride or potassium tert-butoxide in aprotic solvents such as THF or DMF have also been found to be suitable.

The compounds used as starting materials are commercially available or can be prepared by processes known from the literature; 2-substituted thiazole-4-carboxylic esters, for example, can be synthesized by cyclocondensing the corresponding carbothioamides with $BrCH_2COCO_2Et$ (analogously to Sandoz-Patent-GmbH, DE 3443698). An alternative method is the substitution of the bromine atom of ethyl 2-bromo-4-thiazolecarboxylate by amino derivatives (analogously to R. A. Stokbroekx, G. A. J. Grauwels, M. Willems, EP 398425; K. Schiemann, H. Boettcher, H. T. Henning; G. Hoelzemann, C. van Amsterdam, G. Bartoszyk, J. Leibrock, C. Seyfried, WO 2004041815). The corresponding 5-substituted derivatives can be obtained analogously (see K. Anandan, X. Xiao, D. V. Patel, J. S. Ward, US 2005250784).

The compounds of the general formula I are isolated from the reaction mixture and purified by processes known per se, such as extraction, crystallization or chromatography. The examples adduced below serve to illustrate the invention, but without restricting it.

The identity of the compounds was checked by mass spectrometry.

EXAMPLE 1

[5-(5-Benzyloxypyridin-2-yl)-3,4,5,6-tetrahydro-1H-pyrrolo[3,4-c]pyrrol-2-yl](2-trifluoromethylphenyl)methanone

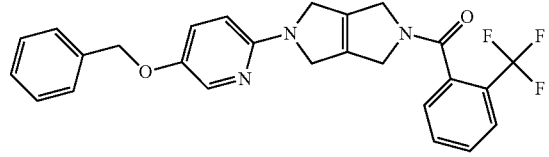 [SMILES: O=C(c1ccccc1C(F)(F)F)N1CC2=C(C1)CN(c1ccc(OCc3ccccc3)cn1)C2]

1a) tert-Butyl 5-(2-trifluoromethylbenzoyl)-3,4,5,6-tetrahydro-1H-pyrrolo[3,4-c]pyrrole-2-carboxylate

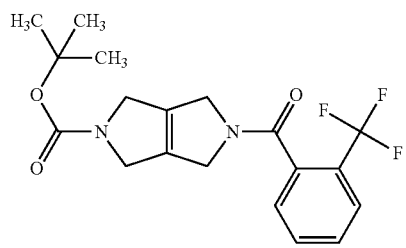 [SMILES: CC(C)(C)OC(=O)N1CC2=C(C1)CN(C(=O)c1ccccc1C(F)(F)F)C2]

tert-Butyl 3,4,5,6-tetrahydro-1H-pyrrolo[3,4-C]pyrrole-2-carboxylate hydrochloride (30 g, 121.6 mmol) was suspended in 700 ml of methylene chloride, triethylamine (50.7 ml, 364.8 mmol) was added with ice bath cooling, and 2-(trifluoromethyl)benzoyl chloride (25.22 ml, 171.2 mmol) was slowly added dropwise. The brown suspension was stirred for 2 h, in the course of which it was allowed to come to RT. The reaction mixture was admixed with water, and the organic phase was removed, dried and concentrated by rotary evaporation. The crude product (56.8 g) was converted further without purification.

1b) (3,4,5,6-Tetrahydro-1H-pyrrolo[3,4-c]pyrrol-2-yl)(2-trifluoromethylphenyl)methanone trifluoroacetate

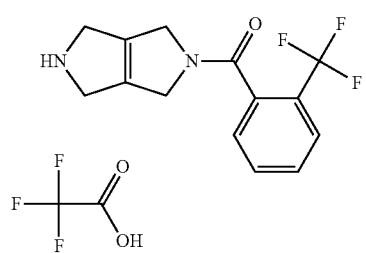 [SMILES: O=C(O)C(F)(F)F ; O=C(c1ccccc1C(F)(F)F)N1CC2=C(CNC2)C1]

tert-Butyl 5-(2-trifluoromethylbenzoyl)-3,4,5,6-tetrahydro-1H-pyrrolo[3,4-c]pyrrole-2-carboxylate (56.8 g) was stirred with 15 ml of 90 percent trifluoroacetic acid at RT for 3 h. The reaction mixture was concentrated and purified by preparative HPLC (PR18, acetonitrile/water 0.1% TFA). Yield: 40.81 g (85%), M+H+: 283.14.

1c) [5-(5-Nitropyridin-2-yl)-3,4,5,6-tetrahydro-1H-pyrrolo[3,4-c]pyrrol-2-yl](2-trifluoromethylphenyl)methanone

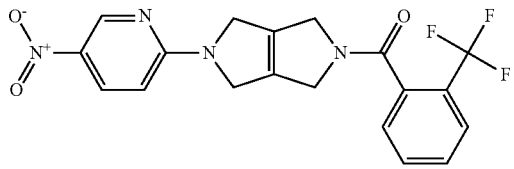 [SMILES: O=C(c1ccccc1C(F)(F)F)N1CC2=C(C1)CN(c1ccc([N+](=O)[O-])cn1)C2]

2-Chloro-5-nitropyridine (510 mg, 3.22 mmol), (3,4,5,6-tetrahydro-1H-pyrrolo[3,4-c]pyrrol-2-yl)(2-trifluoromethylphenyl)methanone trifluoroacetate (1.046 g, 2.64 mmol) and cesium carbonate (1.72 g, 5.28 mmol) were stirred in 20 ml of DMF at 80° C. for 5 h. After concentrating under reduced pressure, ethyl acetate and water were added, and the precipitated solid was filtered off with suction. The organic phase was removed and concentrated. The two precipitates were combined. Yield: 845 mg (79%), M+H+: 405.04.

1d) [5-(5-Aminopyridin-2-yl)-3,4,5,6-tetrahydro-1H-pyrrolo[3,4-c]pyrrol-2-yl]2-trifluoromethylphenyl)methanone acetate

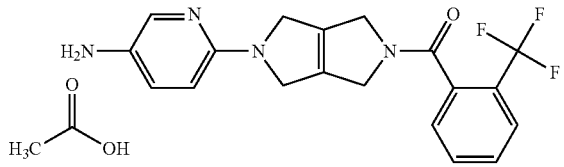

[5-(5-Nitropyridin-2-yl)-3,4,5,6-tetrahydro-1H-pyrrolo[3,4-c]pyrrol-2-yl](2-trifluoromethyl-phenyl)methanone (565 mg, 1.38 mmol) and zinc dust (870 mg, 13.31 mmol) were suspended under an argon atmosphere in 15 ml of methanol. After adding 0.3 ml of acetic acid, the mixture was stirred at RT for 45 min and filtered with suction, and the filtrate was concentrated. The resulting product was converted further without purification.

1e) [5-(5-Hydroxypyridin-2-yl)-3,4,5,6-tetrahydro-1H-pyrrolo[3,4-c]pyrrol-2-yl](2-trifluoromethylphenyl)methanone

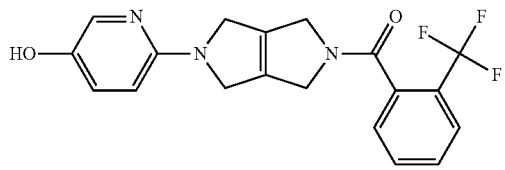

Sodium nitrite (106.1 mg, 1.537 mmol) was dissolved at 0° C. in 1.84 ml of conc. sulfuric acid. Subsequently, [5-(5-aminopyridin-2-yl)-3,4,5,6-tetrahydro-1H-pyrrolo[3,4-c]pyrrol-2-yl](2-trifluoromethylphenyl)methanone acetate (523 mg, 1.2 mmol), dissolved in 8 ml of acetic acid, was added dropwise, the cooling bath was removed and stirring was continued for 1 h. The reaction solution was added dropwise to 50 ml of boiling water and stirred under reflux for 5 h. After cooling, the mixture was admixed with ethyl acetate and filtered off from the residue, the water phase was adjusted to pH 4 with sodium hydrogencarbonate solution, and the organic phase was removed and concentrated. Yield: 181 mg (40%), M+H+: 376.11.

1f) [5-(5-Benzyloxypyridin-2-yl)-3,4,5,6-tetrahydro-1H-pyrrolo[3,4-c]pyrrol-2-yl](2-trifluoro-methylphenyl)methanone

[5-(5-Hydroxypyridin-2-yl)-3,4,5,6-tetrahydro-1H-pyrrolo[3,4-c]pyrrol-2-yl](2-trifluoro-methylphenyl)methanone (175 mg, 0.466 mmol), benzyl bromide (123 µl, 1.12 mmol) and cesium carbonate (364 mg, 1.12 mmol) were stirred at 60° C. for 4 h. After concentrating, water and ethyl acetate were added, and the organic phase was removed, concentrated and purified by preparative HPLC (PR18, acetonitrile/water 0.1% TFA). Yield: 20 mg (9%), M+H+: 466.12.

EXAMPLE 2

{5-[6-(Thiazol-2-ylmethoxy)pyridazin-3-yl]-3,4,5,6-tetrahydro-1H-pyrrolo[3,4-c]pyrrol-2-yl}-(2-trifluoromethylphenyl)methanone

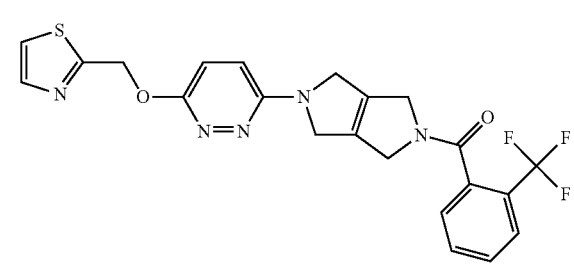 [SMILES: O=C(c1ccccc1C(F)(F)F)N1CC2=C(C1)CN(c1ccc(OCc3nccs3)nn1)C2]

2a) [5-(6-Chloropyridazin-3-yl)-3,4,5,6-tetrahydro-1H-pyrrolo[3,4-c]pyrrol-2-yl](2-trifluoromethylphenyl)methanone

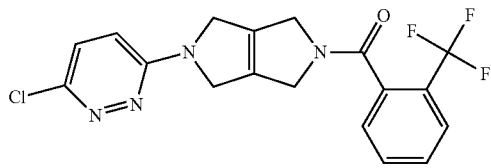 [SMILES: O=C(c1ccccc1C(F)(F)F)N1CC2=C(C1)CN(c1ccc(Cl)nn1)C2]

(3,4,5,6-Tetrahydro-1H-pyrrolo[3,4-c]pyrrol-2-yl)(2-trifluoromethylphenyl)methanone trifluoroacetate (1 g, 2.52 mmol, example 1b) was dissolved in 18 ml of NMP and admixed with potassium tert-butoxide (849 mg, 7.57 mmol). tert-Butanol formed was drawn off on a rotary evaporator, and 3,6-dichloropyridazine (376 mg, 2.52 mmol) was added. The reaction mixture was stirred in a microwave reactor at 100° C. for 10 min. After adding 0.5 eq of 3,6-dichloropyridazine each time, the mixture was stirred twice more at 100° C. for 15 min in the microwave reactor. The residue was admixed with water and ethyl acetate, and the organic phase was removed, concentrated and purified by preparative HPLC (PR18, acetonitrile/water 0.1% TFA). Yield: 669 mg (67%), M+H+: 395.08.

2b) {5-[6-(Thiazol-2-ylmethoxy)pyridazin-3-yl]-3,4,5,6-tetrahydro-1H-pyrrolo[3,4-c]pyrrol-2-yl}-(2-trifluoromethylphenyl)methanone Thiazol-2-ylmethanol (64 mg, 0.56 mmol) was dissolved in 2 ml of anhydrous DMF. After adding sodium hydride (42 mg, 55 percent suspension in oil), the mixture was stirred for 30 min, [5-(6-chloropyridazin-3-yl)-3,4,5,6-tetrahydro-1H-pyrrolo[3,4-c]pyrrol-2-yl](2-trifluoromethylphenyl)methanone (100 mg, 0.25 mmol) was added, and the mixture was stirred at 150° C. for 30 h. After concentrating, water and ethyl acetate were added, and the organic phase was removed, concentrated and purified by preparative HPLC (PR18, acetonitrile/water 0.1% TFA). Yield: 6 mg (5%), M+H+: 474.01.

EXAMPLE 3

[5-(6-Benzyloxpyridazin-3-yl)-3,4,5,6-tetrahydro-1H-pyrrolo[3,4-c]pyrrol-2-yl](2-trifluoromethylphenyl)methanone

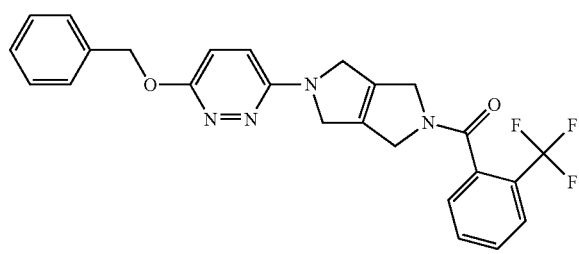 [SMILES: O=C(c1ccccc1C(F)(F)F)N1CC2=C(C1)CN(c1ccc(OCc3ccccc3)nn1)C2]

[5-(6-Chloropyridazin-3-yl)-3,4,5,6-tetrahydro-1H-pyrrolo[3,4-c]pyrrol-2-yl](2-trifluoromethylphenyl)methanone (2.5 g, 6.33 mmol) was reacted analogously to example 2b in N-methylpyrrolidinone with benzyl alcohol and potassium tert-butoxide. Yield: 357 mg (12%), M+H+: 467.15.

EXAMPLE 4

[5-(6-Phenethyloxypyridazin-3-yl)-3,4,5,6-tetrahydro-1H-pyrrolo[3,4-c]pyrrol-2-yl](2-trifluoromethylphenyl)methanone trifluoroacetate

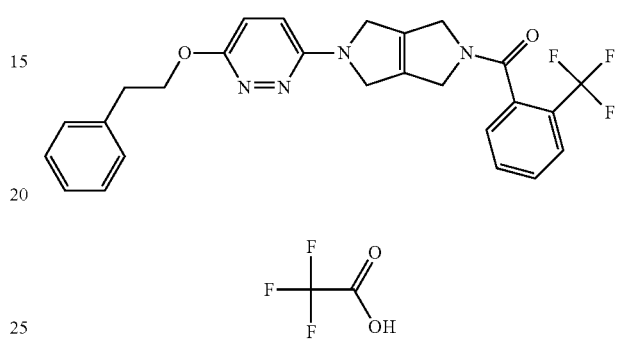

4a) 3-Chloro-6-phenethyloxypyridazine

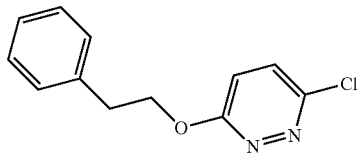 [SMILES: Clc1ccc(OCCc2ccccc2)nn1]

3,6-Dichloropyridazine (1.0 g, 6.712 mmol), 2-phenylethanol (820 mg, 6.712 mmol) and sodium hydride (60 percent suspension in oil, 268 mg, 6.712 mmol) were stirred in 25 ml of N-methylpyrrolidin-2-one at room temperature for 30 minutes. After concentrating, water and ethyl acetate were added, and the organic phase was removed, concentrated and purified by preparative HPLC (PR18, acetonitrile/water 0.1% TFA). Yield: 878 mg (56%), M+H+: 235.1.

4b) [5-(6-Phenethyloxypyridazin-3-yl)-3,4,5,6-tetrahydro-1H-pyrrolo[3,4-c]pyrrol-2-yl](2-trifluoromethylphenyl)methanone trifluoroacetate (3,4,5,6-Tetrahydro-1H-pyrrolo[3,4-c]pyrrol-2-yl)(2-trifluoromethylphenyl)methanone trifluoroacetate (example 1b) (500 mg, 1.26 mmol), 3-chloro-6-phenethyloxypyridazine (example 4a) (296 mg, 1.26 mmol), tris(dibenzylideneacetone)dipalladium(0)chloroform adduct (67.9 mg, 65.6 µmol), (R)-(+)-2,2'-bis(diphenylphosphino)-1,1'-binaphthyl (81.7 mg, 131 µmol) and cesium carbonate (1.645 g, 5.048 mmol) were stirred in 5 ml of dioxane under an argon atmosphere at 80° C. for 4 h. The reaction mixture was concentrated and admixed with ethyl acetate and water, and the organic phase was removed, concentrated and purified by preparative HPLC (PR18, acetonitrile/water 0.1% TFA). Yield: 104 mg (14%), M+H+: 481.2.

EXAMPLE 5

{5-[6-(2-Cyclopropylethoxy)pyridazin-3-yl]-3,4,5,6-tetrahydro-1H-pyrrolo[3,4-c]pyrrol-2-yl}-(2-trifluoromethylphenyl)methanone trifluoroacetate

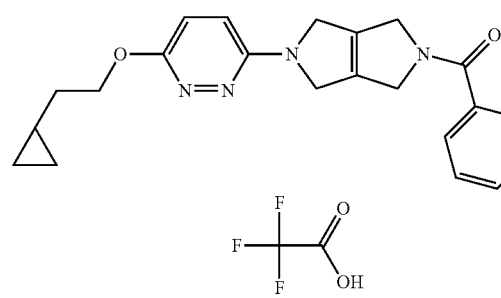

5a) 3-Chloro-6-(2-cyclopropylethoxy)pyridazine

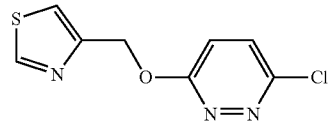 [SMILES: Clc1ccc(OCc2cscn2)nn1]

3,6-Dichloropyridazine (1.0 g, 6.712 mmol) was reacted analogously to example 4a with 2-cyclopropylethanol (578 mg, 6.712 mmol). Yield: 519 mg (39%), M+H+: 199.1. 5b) {5[6-(2-Cyclopropylethoxy)pyridazin-3-yl]-3,4,5,6-tetrahydro-1H-pyrrolo[3,4-c]pyrrol-2-yl}-(2-trifluoromethylphenyl)methanone trifluoroacetate (3,4,5,6-Tetrahydro-1H-pyrrolo[3,4-c]pyrrol-2-yl)(2-trifluoromethylphenyl)methanone trifluoroacetate (example 1b) (500 mg, 1.26 mmol) was reacted analogously to example 4b with 3-chloro-6-(2-cyclopropylethoxy)pyridazine (250.7 mg, 1.26 mmol). Yield: 182 mg (26%), M+H+: 445.14.

EXAMPLE 6

{5-[6-(Thiazol-4-ylmethoxy)pyridazin-3-yl]-3,4,5,6-tetrahydro-1H-pyrrolo[3,4-c]pyrrol-2-yl}-(2-trifluoromethylphenyl)methanone trifluoroacetate

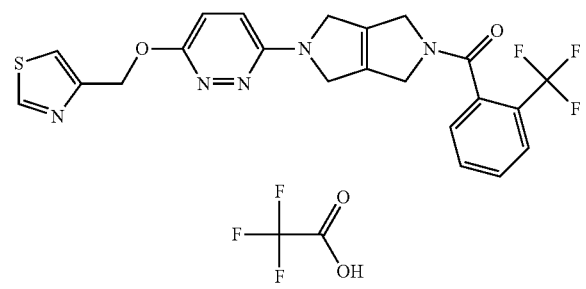

6a) 3-Chloro-6-(thiazol-4-ylmethoxy)pyridazine

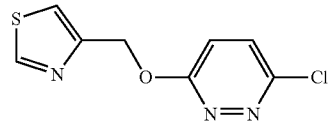 [SMILES: Clc1ccc(OCc2cscn2)nn1]

3,6-Dichloropyridazine (1.0 g, 6.712 mmol) was reacted analogously to example 4a with thiazol-4-ylmethanol (578 mg, 6.712 mmol). Yield: 775 mg (51%), M+H+: 228.0, 6b) {5-[6-(Thiazol-4-ylmethoxy)pyridazin-3-yl]-3,4,5,6-tetrahydro-1H-pyrrolo[3,4-c]pyrrol-2-yl}-(2-trifluoromethylphenyl)methanone trifluoroacetate (3,4,5,6-Tetrahydro-1H-pyrrolo[3,4-c]pyrrol-2-yl)(2-trifluoromethylphenyl)methanone trifluoroacetate (example 1b) (500 mg, 1.26 mmol) was reacted analogously to example 4b with 3-chloro-6-(thiazol-4-ylmethoxy)pyridazine (287.3 mg, 1.26 mmol). Yield: 36 mg (5%), M+H+: 474.26.

EXAMPLE 7

{5-[6-(Tetrahydropyran-4-ylmethoxy)pyridazin-3-yl]-3,4,5,6-tetrahydro-1H-pyrrolo[3,4-c]pyrrol-2-yl}-(2-trifluoromethylphenyl)methanone trifluoroacetate

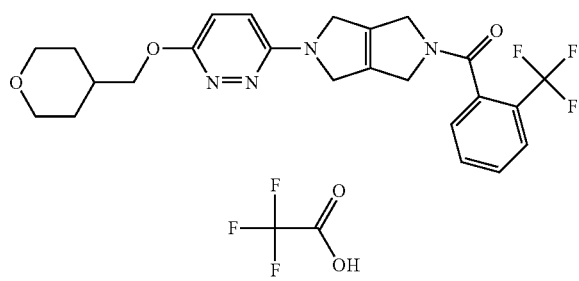

7a) 3-Chloro-6-(tetrahydropyran-4-ylmethoxy)pyridazine

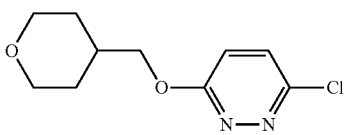 [SMILES: Clc1ccc(OCC2CCOCC2)nn1]

3,6-Dichloropyridazine (1.0 g, 6.712 mmol) was reacted analogously to example 4a with (tetrahydropyran-4-yl)methanol (779 mg, 6.712 mmol). Yield: 683 mg (45%), M+H+: 229.1.

7b) {5-[6-(Tetrahydropyran-4-ylmethoxy)pyridazin-3-yl]-3,4,5,6-tetrahydro-1H-pyrrolo[3,4-c]pyrrol-2-yl}-(2-trifluoromethylphenyl)methanone trifluoroacetate (3,4,5,6-Tetrahydro-1H-pyrrolo[3,4-c]pyrrol-2-yl)(2-trifluoromethylphenyl)methanone trifluoroacetate (example 1b)

(500 mg, 1.26 mmol) was reacted analogously to example 4b with 3-chloro-6-(tetrahydropyran-4-ylmethoxy)pyridazine (288.6 mg, 1.26 mmol). Yield: 129 mg (17%), M+H+: 475.18.

EXAMPLE 8

5-(6-Benzyloxypyridazin-3-yl)-3,4,5,6-tetrahydro-1H-pyrrolo[3,4-c]pyrrol-2-yl](2-trifluoromethylphenyl)methanone hydrochloride

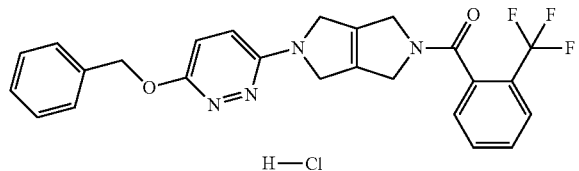

8a) 3-Benzyloxy-6-chloropyridazine

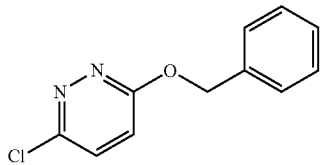 [SMILES: Clc1ccc(OCc2ccccc2)nn1]

3,6-Dichloropyridazine (10.0 g, 67.12 mmol) was reacted analogously to example 4a with benzyl alcohol (6.95 ml, 67.12 mmol). Yield: 12.82 g (87%), M+H+: 221.1.

8b) 5-(6-Benzyloxpyridazin-3-yl)-3,4,5,6-tetrahydro-1H-pyrrolo[3,4-c]pyrrol-2-yl](2-trifluoromethylphenyl)methanone hydrochloride (3,4,5,6-Tetrahydro-1H-pyrrolo[3,4-c]pyrrol-2-yl)(2-trifluoromethylphenyl)methanone trifluoroacetate (example 1b) (5.0 g, 12.62 mmol) was stirred analogously to example 4b with 3-benzyloxy-6-chloropyridazine (2.785 g, 12.62 mmol) at 100° C. for 8 h. The reaction mixture was diluted with methanol and filtered, and the filtrate was concentrated. The residue of the filtrate was suspended in 2 N hydrochloric acid and admixed with ethyl acetate, and the residue formed was filtered off with suction and dried. Yield: 3.0 g (47%), M+H+: 467.15.

EXAMPLE 9

5-[6-(Pyridin-2-ylmethoxy)pyridazin-3-yl]-3,4,5,6-tetrahydro-1H-pyrrolo[3,4-c]pyrrol-2-yl}-(2-trifluoromethylphenyl)methanone hydrochloride

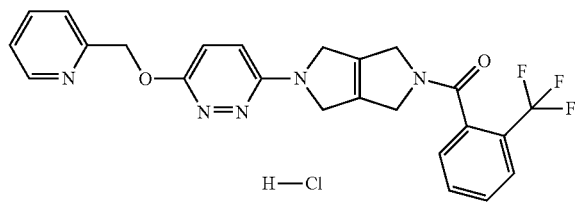

9a) 3-Chloro-6-(pyridin-2-ylmethoxy)pyridazine

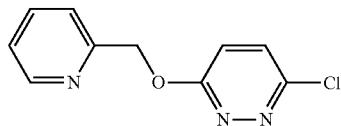 [SMILES: Clc1ccc(OCc2ccccn2)nn1]

3,6-Dichloropyridazine (1.0 g, 6.712 mmol) was reacted analogously to example 4a with 2-hydroxymethylpyridine (732 mg, 6.712 mmol). Yield: 1.26 g (85%), M+H+: 222.1.

9b) 5-[6-(Pyridin-2-ylmethoxy)pyridazin-3-yl]-3,4,5,6-tetrahydro-1H-pyrrolo[3,4-c]pyrrol-2-yl}(2-trifluoromethylphenyl)methanone trifluoroacetate (3,4,5,6-Tetrahydro-1H-pyrrolo[3,4-c]pyrrol-2-yl)(2-trifluoromethylphenyl)methanone trifluoroacetate (example 1b) (1 g, 2.52 mmol) was reacted analogously to example 4b with 3-chloro-6-(pyridin-2-ylmethoxy)pyridazine (559 mg, 2.52 mmol). In the course of extraction, the unprotonated compound precipitated out. The substance was filtered off with suction, admixed with dilute hydrochloric acid and lyophilized. Yield: 36 mg (3%), M+H+: 468.2.

The invention claimed is:
1. A compound of the formula I

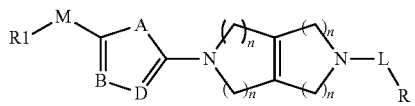

in which

R is hydrogen, $(C_1-C_{16})$-alkyl, $(C_1-C_5)$-alkyloxy, $(C_1-C_5)$-alkylthio, $(C_1-C_5)$-alkylamino, di-$(C_2-C_8)$-alkylamino, $(C_0-C_4)$-alkylene-$(C_6-C_{10})$-aryl, $(C_0-C_4)$-alkylene-$(C_5-C_{12})$-heteroaryl, $(C_0-C_4)$-alkylene-$(C_3-C_{12})$-heterocyclyl, $(C_0-C_4)$-alkylene-$(C_3-C_{12})$-cycloalkyl, a bicyclic $(C_8-C_{14})$ ring system, where aryl, heteroaryl, heterocyclyl, cycloalkyl or the bicyclic $(C_8-C_{14})$ ring system may be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl or aminosulfonyl;

R1 is hydrogen, $(C_1-C_{10})$-alkyl, 13 $(C_6-C_{10})$-aryl, —$(C_5-C_{12})$-heteroaryl, —$(C_3-C_{12})$-heterocyclyl, —$(C_3-C_{12})$-cycloalkyl;

where alkyl may be substituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, —$(C_6-C_{10})$-aryl, —$(C_5-C_{12})$-heteroaryl, —$(C_3-C_{12})$-heterocyclyl or —$(C_3-C_{12})$-cycloalkyl, where aryl, heteroaryl, heterocyclyl or cycloalkyl may optionally be mono- or polysubstituted by halogen, $(C_1-C_6)$-alkyl, $(C_1-C_3)$-alkyloxy, hydroxyl, ($C_1$-$C_6$)-alkylmercapto, amino, ($C_1$-$C_6$)-alkylamino, di-($C_2$-$C_{12}$)-alkylamino;

R2 is hydrogen, ($C_1$-$C_{16}$)-alkyl, ($C_0$-$C_4$)-alkylene-($C_6$-$C_{10}$)-aryl;

R3 is hydrogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino, cyano, ($C_1$-$C_6$)-alkylcarbonyl, halogen, trifluoromethyl, trifluoromethyloxy, ($C_1$-$C_6$)-alkylsulfonyl, aminosulfonyl;

A is O, S, N(R2), C(R3), C(R3)=C(R3);
B is C(R3), N;
D is C(R3), N;
where at least one of the members A, B or D must be nitrogen;
n is 1;
L is a bond, —C(=O)—, —C(=S)—, —C(=O)—N(R2)-, —C(=O)—O—, —S(O)$_{0-2}$—, —S(O)$_{0-2}$—N(R2)-, a mono- or bicyclic ring system in which one or more ring members may be N(R3), O, S or —C(=O)—;
M is —O—, —CH$_2$—O—, —O—CH$_2$—;
and physiologically compatible salts thereof.

2. A compound of the formula Ia

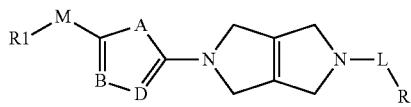

in which

R is hydrogen, ($C_1$-$C_{16}$)-alkyl, ($C_1$-$C_5$)-alkyloxy, ($C_1$-$C_5$)-alkylthio, ($C_1$-$C_5$)-alkylamino, di-($C_2$-$C_8$)-alkylamino, ($C_0$-$C_4$)-alkylene-($C_6$-$C_{10}$)-aryl, ($C_0$-$C_4$)-alkylene-($C_5$-$C_{12}$)-heteroaryl, ($C_0$-$C_4$)-alkylene-($C_3$-$C_{12}$)-heterocyclyl, ($C_0$-$C_4$)-alkylene-($C_3$-$C_{12}$)-cycloalkyl, a bicyclic ($C_8$-$C_{14}$) ring system,
where aryl, heteroaryl, heterocyclyl, cycloalkyl or the bicyclic ($C_8$-$C_{14}$) ring system may be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino, mono-($C_1$-$C_6$)-alkylaminocarbonyl, di-($C_2$-$C_8$)-alkylaminocarbonyl, ($C_1$-$C_6$)-alkoxycarbonyl, ($C_1$-$C_6$)-alkylcarbonyl, cyano, trifluoromethyl, trifluoromethyloxy, ($C_1$-$C_6$)-alkylsulfonyl or aminosulfonyl;

R1 is ($C_1$-$C_{10}$)-alkyl, ($C_0$-$C_4$)-alkylene-($C_6$-$C_{10}$)-aryl; ($C_0$-$C_4$)-alkylene-($C_5$-$C_{12}$)-heteroaryl, —($C_3$-$C_{12}$)-heterocyclyl, —($C_3$-$C_{12}$)-cycloalkyl,
where alkyl may be substituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino, —($C_6$-$C_{10}$)-aryl, —($C_5$-$C_{12}$)-heteroaryl, —($C_3$-$C_{12}$)-heterocyclyl or —($C_3$-$C_{12}$)-cycloalkyl,
where aryl, heteroaryl, heterocyclyl or cycloalkyl may optionally be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino;

R2 is hydrogen, ($C_1$-$C_{16}$)-alkyl, ($C_0$-$C_4$)-alkylene-($C_6$-$C_{10}$)-aryl;

R3 is hydrogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino, cyano, ($C_1$-$C_6$)-alkylcarbonyl, halogen, trifluoromethyl, trifluoromethyloxy, ($C_1$-$C_6$)-alkylsulfonyl, aminosulfonyl;

A is O, S, N(R2), C(R3), C(R3)=C(R3);
B is C(R3), N;
D is C(R3), N;
where at least one of the members A, B or D must be nitrogen;
L is a bond, —C(=O)—, —C(=S)—, —C(=O)—N(R2)-, —C(=O)—O—, —S(O)$_{0-2}$—, —S(O)$_{0-2}$—N(R2)-, a mono- or bicyclic ring system in which one or more ring members may be N(R3), O, S or —C(=O)—;
M is —O—, —O—CH$_2$—;
and physiologically compatible salts thereof.

3. A compound of the formula Ia as claimed in claim 2, wherein

R is hydrogen, ($C_1$-$C_{16}$)-alkyl, ($C_1$-$C_5$)-alkyloxy, ($C_1$-$C_5$)-alkylthio, ($C_1$-$C_5$)-alkylamino, di-($C_2$-$C_8$)-alkylamino, ($C_0$-$C_4$)-alkylene-($C_6$-$C_{10}$)-aryl, ($C_0$-$C_4$)-alkylene-($C_5$-$C_{12}$)-heteroaryl, ($C_0$-$C_4$)-alkylene-($C_3$-$C_{12}$)-heterocyclyl, ($C_0$-$C_4$)-alkylene-($C_3$-$C_{12}$)-cycloalkyl, a bicyclic ($C_8$-$C_{14}$) ring system,
where aryl, heteroaryl, heterocyclyl, cycloalkyl or the bicyclic ($C_8$-$C_{14}$) ring system may be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino, mono-($C_1$-$C_6$)-alkylaminocarbonyl, di-($C_2$-$C_8$)-alkylaminocarbonyl, ($C_1$-$C_6$)-alkoxycarbonyl, ($C_1$-$C_6$)-alkylcarbonyl, cyano, trifluoromethyl, trifluoromethyloxy, ($C_1$-$C_6$)-alkylsulfonyl or aminosulfonyl;

R1 is ($C_1$-$C_{10}$)-alkyl, ($C_0$-$C_4$)-alkylene-($C_6$-$C_{10}$)-aryl, ($C_0$-$C_4$)-alkylene-($C_5$-$C_{12}$)-heteroaryl, —($C_3$-$C_{12}$)-heterocyclyl, —($C_3$-$C_{12}$)-cycloalkyl,
where alkyl may be substituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino, —($C_6$-$C_{10}$)-aryl, —($C_5$-$C_{12}$)-heteroaryl, —($C_3$-$C_{12}$)-heterocyclyl or —($C_3$-$C_{12}$)-cycloalkyl,
where aryl, heteroaryl, heterocyclyl or cycloalkyl may optionally be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino;

R2 is hydrogen, ($C_1$-$C_{16}$)-alkyl, ($C_0$-$C_4$)-alkylene-($C_6$-$C_{10}$)-aryl;

R3 is hydrogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino, cyano, ($C_1$-$C_6$)-alkylcarbonyl, halogen, trifluoromethyl, trifluoromethyloxy, ($C_1$-$C_6$)-alkylsulfonyl, aminosulfonyl;

A is S, C(R3)=C(R3);
B is C(R3), N;
D is N;
L is a bond, —C(=O)—, —C(=S)—, —C(=O)—N(R2)-, —C(=O)—O—, —S(O)$_{0-2}$—, —S(O)$_{0-2}$—N(R2)-, a mono- or bicyclic ring system in which one or more ring members may be N(R3), O, S or —C(=O)—;
M is —O—, —O—CH$_2$;
and physiologically compatible salts thereof.

4. A compound of the formula Ia as claimed in claim 2, wherein

R is ($C_1$-$C_{16}$)-alkyl, ($C_1$-$C_5$)-alkyloxy, ($C_0$-$C_4$) -alkylene-($C_6$-$C_{10}$)-aryl, a bicyclic ($C_8$-$C_{14}$) ring system,
where aryl or the bicyclic ($C_8$-$C_{14}$) ring system may be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino, mono-($C_1$-$C_6$)-alkylaminocarbonyl, di-($C_2$-$C_8$)-alkylaminocarbonyl, ($C_1$-$C_6$)-alkoxycarbonyl, ($C_1$-

$C_6$)-alkylcarbonyl, cyano, trifluoromethyl, trifluoromethyloxy, ($C_1$-$C_6$)-alkylsulfonyl or aminosulfonyl;

R1 is ($C_1$-$C_{10}$-alkyl, ($C_0$-$C_4$)-alkylene-($C_6$-$C_{10}$)-aryl, ($C_0$-$C_4$-alkylene-($C_5$-$C_{12}$)-heteroaryl, —($C_3$-$C_{12}$)-heterocyclyl, —($C_3$-$C_{12}$)-cycloalkyl, where alkyl may be substituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino, —($C_6$-$C_{10}$)-aryl, —($C_5$-$C_{12}$)-heteroaryl, —($C_3$-$C_{12}$)-heterocyclyl or —($C_3$-$C_{12}$)=cycloalkyl, where aryl, heteroaryl, heterocyclyl or cycloalkyl may optionally be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino;

R2 is hydrogen, ($C_1$-$C_6$)-alkyl, ($C_0$-$C_4$)-alkylene-($C_6$-$C_{10}$)-aryl;

R3 is hydrogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino, cyano, ($C_1$-$C_6$)-alkylcarbonyl, halogen, trifluoromethyl, trifluoromethyloxy, ($C_1$-$C_6$)-alkylsulfonyl, aminosulfonyl;

A is S, C(R3)=C(R3);
B is C(R3), N;
D is N;
L is a bond, —C(=O)—:
M is —O—;
and physiologically compatible salts thereof.

5. A compound of the formula Ia as claimed in claim 2, wherein

R is ($C_0$-$C_4$)-alkylene-($C_6$-$C_{10}$)-aryl,
where aryl may be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino, mono-($C_1$-$C_6$)-alkylaminocarbonyl, di-($C_2$-$C_8$)-alkylaminocarbonyl, ($C_1$-$C_6$)-alkoxycarbonyl, ($C_1$-$C_6$)-alkylcarbonyl, cyano, trifluoromethyl, trifluoromethyloxy, ($C_1$-$C_6$)-alkylsulfonyl or aminosulfonyl;

R1 is ($C_0$-$C_4$)-alkylene-($C_6$-$C_{10}$)-aryl, ($C_0$-$C_4$)-alkylene-($C_5$-$C_{12}$)-heteroaryl,
where aryl or heteroaryl may optionally be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino;

R3 is hydrogen;
A is C(R3)=C(R3);
B is C(R3), N;
D is N;
L is —C(=O)—:
M is —O—;
and physiologically compatible salts thereof.

6. A compound of the formula Iaa

Iaa

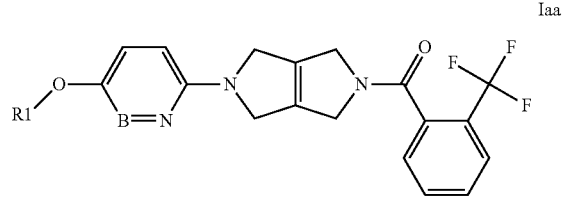

in which
R1 is ($C_0$-$C_4$)-alkylene-($C_6$-$C_{10}$)-aryl, ($C_0$-$C_4$)-alkylene-($C_5$-$C_{12}$)-heteroaryl,
where aryl or heteroaryl may optionally be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino;

B is CH, N;
and physiologically compatible salts thereof.

7. A compound of the formula Iaa as claimed in claim 6, wherein
R1 is ($C_1$-$C_4$)-alkylenephenyl, ($C_1$-$C_4$)-alkylene-($C_5$-$C_6$)-heteroaryl, where heteroaryl is a monocyclic aromatic ring with one or two ring heteroatoms selected from N, O or S and
where phenyl or heteroaryl may optionally be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, di-($C_2$-$C_{12}$)-alkylamino;

B is CH, N;
and physiologically compatible salts thereof.

8. A pharmaceutical composition comprising one or more compounds as claimed in claim 1, 2 or 6 and a pharmaceutically compatible carrier and/or assistant.

9. The pharmaceutical composition according to claim 8, further comprising at least one active ingredient.

10. The pharmaceutical composition as claimed in claim 9, wherein said active ingredient is chosen from the group consisting of one or more antidiabetics, active hypoglycemic ingredients, HMG-CoA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, α-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose 1,6-biphosphatase, modulators of glucose transporter 4, inhibitors of glutamine:fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, modulators of GPR40, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART agonists, NPY agonists, MC4 agonists, orexin agonists, H3 agonists, TNF agonists, CRF agonists, CRF BP antagonists, urocortin agonists, β3 agonists, CB 1 receptor antagonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, decoupling protein 2 or 3 modulators, leptin agonists, DA agonists (bromocriptin, doprexin), lipase/amylase inhibitors, PPAR modulators, RXR modulators, TR-β-agonists and amphetamines.

11. A process for producing a pharmaceutical comprising one or more of the compounds as claimed in claim 1, 2 or 6, which comprises mixing the active ingredient with a pharmaceutically suitable carrier and bringing this mixture into a form suitable for administration.

* * * * *

UNITED STATES PATENT AND TRADEMARK OFFICE
CERTIFICATE OF CORRECTION

PATENT NO. : 8,673,917 B2  
APPLICATION NO. : 13/063088  
DATED : March 18, 2014  
INVENTOR(S) : Zoller et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 143 days.

Signed and Sealed this

Twenty-ninth Day of September, 2015

Michelle K. Lee
*Director of the United States Patent and Trademark Office*